US010677797B2

(12) United States Patent
Hsu

(10) Patent No.: US 10,677,797 B2
(45) Date of Patent: Jun. 9, 2020

(54) ASSAYS AND METHODS FOR DETECTING MYCOBACTERIAL INFECTIONS

(71) Applicant: S&R Pharmaceuticals, LLC, Lenox, MA (US)

(72) Inventor: Tsungda Hsu, Lenox, MA (US)

(73) Assignee: S&R PHARMACEUTICALS, LLC, Lenox, MA (US)

( * ) Notice: Subject to any disclaimer, the term of this patent is extended or adjusted under 35 U.S.C. 154(b) by 0 days.

(21) Appl. No.: 16/083,807

(22) PCT Filed: Mar. 10, 2017

(86) PCT No.: PCT/US2017/021873

§ 371 (c)(1),
(2) Date: Sep. 10, 2018

(87) PCT Pub. No.: WO2017/156436

PCT Pub. Date: Sep. 14, 2017

(65) Prior Publication Data

US 2019/0137492 A1 May 9, 2019

Related U.S. Application Data

(60) Provisional application No. 62/307,393, filed on Mar. 11, 2016.

(51) Int. Cl.

| | |
|---|---|
| ***A61K 39/04*** | (2006.01) |
| ***C12Q 1/00*** | (2006.01) |
| ***G01N 33/53*** | (2006.01) |
| ***G01N 33/569*** | (2006.01) |
| ***G01N 33/558*** | (2006.01) |
| ***C12Q 1/689*** | (2018.01) |

(52) U.S. Cl.

CPC ......... *G01N 33/5695* (2013.01); *C12Q 1/689* (2013.01); *G01N 33/558* (2013.01); *G01N 2469/10* (2013.01); *G01N 2800/26* (2013.01)

(58) Field of Classification Search

CPC ........ A61K 39/00; A61K 39/02; A61K 39/04; C12Q 1/00; C12Q 1/69; G01N 33/00; G01N 33/48; G01N 33/53; G01N 33/569; G01N 33/56944

USPC ............. 424/184.1, 234.1, 248.1; 435/4, 6.1, 435/6.15, 7.1, 7.2

See application file for complete search history.

(56) References Cited

FOREIGN PATENT DOCUMENTS

| | | |
|---|---|---|
| WO | WO 2003/070981 A2 | 8/2003 |
| WO | WO 2011/148269 A2 | 12/2011 |
| WO | WO 2017/156436 A1 | 9/2017 |

OTHER PUBLICATIONS

International Search Report and Written Opinion for Int'l Application No. PCT/US2017/021873, entitled "Assays and Methods for Detecting Mycobacterial Infections," consisting of 12 pages. dated Sep. 11, 2018.

Reddington, K., et al: "Novel Multiplex Real-Time PCR Diagnostic Assay for Identification and Differentiation of *Mycobacterium tuberculosis, Mycobacterium canettii*, and *Mycobacterium tuberculosis* Complex Strains", Journal of Clinical Microbiology, vol. 49, No. 2, pp. 651-657 (2010).

Warren R. M., et al: "Differentiation of *Mycobacterium tuberculosis* Complex by PCR Amplification of Genomic Regions of Difference", International Journal of Tuberculosis and Lung Disease, International Union Against Tuberculosis and Lung Disease, France, vol. 10, No. 7, pp. 818-822 (2006).

Daffe M., et al: "Novel Type-Specific Lipooligosaccharides From *Mycobacterium-tuberculosis*," Biochemistry, American Chemical Society, vol. 30, No. 2, pp. 378-388 (1991).

George R., et al: "Determination of Protein by Coomassie Dye-Binding in Agarose Gels," Journal of Biochemical and Biophysical Methods, Amsterdam, vol. 13, No. 4-5, pp. 221-229 (1986).

Minnikin D., et al: "Review the Methyl-Branched Fortifications of *Mycobacterium tuberculosis*," Chemistry & Biology, vol. 9, No. 5, pp. 545-553, (2002).

Crick, D. C., et al: "Genetics of Capsular Polysaccharides and Cell Envelope (Glyco)Lipids", Microbiology Spectrum, vol. 2, No. 4 (2014).

International Search Report and Written Opinion for Int'l Application No. PCT/US2017/021873, entitled "Assays and Methods for Detecting Mycobacterial Infections," consisting of 6 pages. dated Jul. 3, 2017.

*Primary Examiner* — Rodney P Swartz

(74) *Attorney, Agent, or Firm* — Hamilton, Brook, Smith & Reynolds, P.C.

(57) ABSTRACT

Provided herein is an assay for detecting a rough-type *mycobacterium* and a smooth-type *mycobacterium* in a sample, wherein the *mycobacterium* is *Mycobacterium tuberculosis* or *Mycobacterium bovis*. The assay comprises a first molecule that selectively binds to the rough-type *mycobacterium* or binds to a molecule preferentially secreted by the rough-type *mycobacterium* and a second molecule that selectively binds to the smooth-type *mycobacterium* or binds to a molecule preferentially secreted by the smooth-type *mycobacterium*. The first molecule and the second molecule are independently detectable. Also provided herein are corresponding methods for detecting a rough-type *mycobacterium* and a smooth-type *mycobacterium* in a sample and assays and methods for detecting tuberculosis infection in a sample.

19 Claims, 11 Drawing Sheets

FIG. 2A
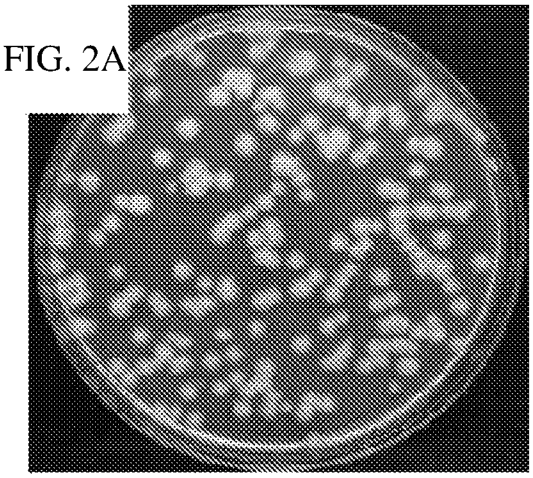
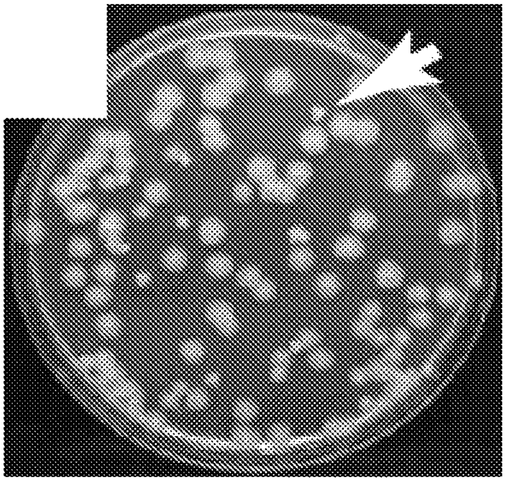
FIG. 2B
FIG. 2C
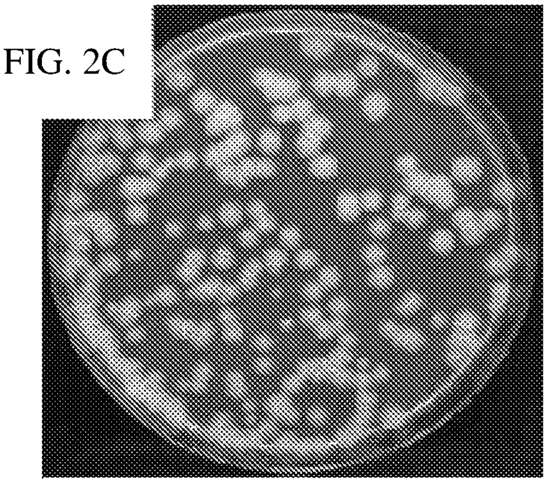
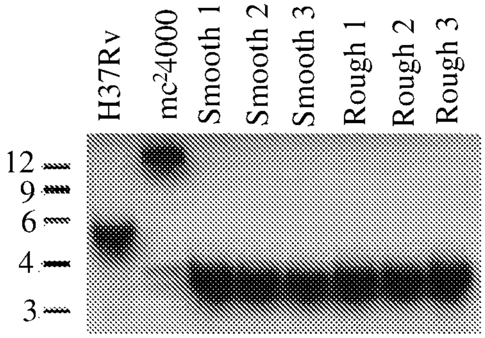
FIG. 2D
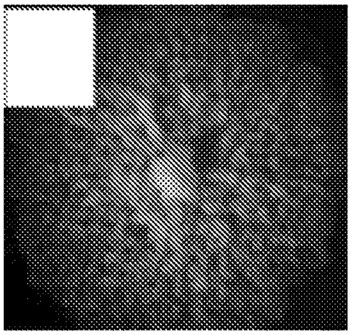
FIG. 2E
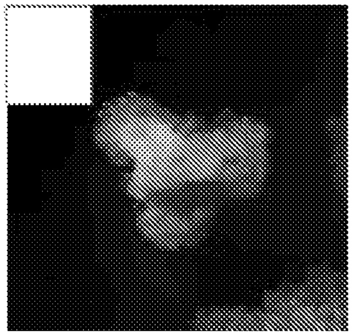
FIG. 2F
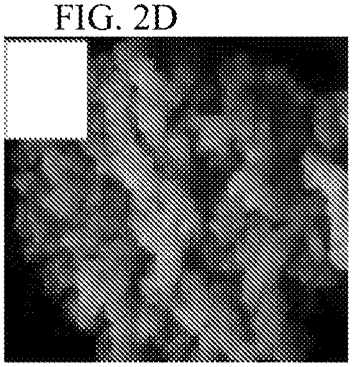
FIG. 2G

ASSAYS AND METHODS FOR DETECTING MYCOBACTERIAL INFECTIONS

RELATED APPLICATION

This application is the U.S. National Stage of International Application No. PCT/US2017/021873, filed on Mar. 10, 2017, published in English, which claims the benefit of U.S. Provisional Application No. 62/307,393, filed on Mar. 11, 2016. The entire teachings of these applications are incorporated herein by reference.

BACKGROUND

Tuberculosis (TB), an infectious disease caused by *Mycobacterium tuberculosis* (*M. tuberculosis*, Mtb), kills more than a million people a year; it is the deadliest infection of humans. Accurate and timely diagnosis of TB is critical for the treatment of patients and prevention of spread of the disease. However, conventional diagnostic tools available to countries with endemic TB suffer from low specificity and low sensitivity. False positivity and false negativity from tuberculin skin test (TST) and sputum smear microscopy have increased the burden in countries where resources are constrained. Definitive diagnosis relies on the growth of TB culture inoculated with sputum obtained from patients suspected of active TB infection. It is a lengthy process normally taking up to two months to reach diagnosis. Modern technology has improved the TB diagnosis in accuracy and decreased the turnaround time, but requires sophisticated equipment and specially trained personnel, which diminishes its practical uses in countries with TB epidemics.

Detection of TB during latent infection is a special problem because during latent infection, Mtb is not present in the sputum. Currently, there is no test to tell if someone is latently infected with TB. Thus, the current skin and blood tests can only tell whether a person has been exposed to TB, but not if they are latently infected.

Accordingly, there is a need to develop a diagnostic tool for active human TB that is accurate, highly sensitive and specific, rapid, cost-effective and simple to use, such that it can be deployed in point-of-care clinics, especially in resource-constrained countries. In addition, there is a clear need for a diagnostic method to determine whether a person is latently infected with TB.

SUMMARY OF THE INVENTION

The present invention is based, in part, on the discovery of phase variation in Mtb and the hypothesis that phase variation plays a role in Mtb pathogenesis. More specifically, the inventors discovered that Mtb exhibits at least two distinct morphotypes, a rough or raised (R) morphotype and a smooth or spread (S) morphotype, which are characterized by distinct cell surface morphologies and gene expression profiles and undergo reversible phase transition upon plating on agar. The assays and methods described herein exploit the discovery of the significance and applications of phase variation in Mtb to provide improved diagnostic tools for human TB that overcome some of the drawbacks of existing methods.

Accordingly, a first embodiment is an assay for detecting a rough-type *mycobacterium* and a smooth-type *mycobacterium* in a sample, wherein the *mycobacterium* is *Mycobacterium tuberculosis* or *Mycobacterium bovis*. The assay comprises a first molecule that selectively binds to the rough-type *mycobacterium* or binds to a molecule preferentially secreted by the rough-type *mycobacterium* and a second molecule that selectively binds to the smooth-type *mycobacterium* or binds to a molecule preferentially secreted by the smooth-type *mycobacterium*. The first molecule and the second molecule are independently detectable.

A second embodiment is an assay for detecting tuberculosis infection in a sample. The assay comprises a first molecule that selectively binds to rough-type *Mycobacterium tuberculosis* or binds to a molecule preferentially secreted by rough-type *Mycobacterium tuberculosis* and a second molecule that selectively binds to smooth-type *Mycobacterium tuberculosis* or binds to a molecule preferentially secreted by smooth-type *Mycobacterium tuberculosis*. The first molecule and the second molecule are independently detectable. Active tuberculosis infection is indicated by presence of rough-type *Mycobacterium tuberculosis*, as signaled by detection of the first molecule, and presence of smooth-type *Mycobacterium tuberculosis*, as signaled by detection of the second molecule. Latent tuberculosis infection is indicated by presence of rough-type *Mycobacterium tuberculosis*, as signaled by detection of the first molecule, and absence of smooth-type *Mycobacterium tuberculosis*, as signaled by detection of the second molecule.

A third embodiment is a sputum-smear assay for detecting a rough-type *mycobacterium* and a smooth-type *mycobacterium* in a sample, wherein the *mycobacterium* is *Mycobacterium tuberculosis* or *Mycobacterium bovis* and is immobilized on a surface. The assay comprises a first molecule that selectively binds to the rough-type *mycobacterium* and a second molecule that selectively binds to the smooth-type *mycobacterium*. The first molecule and the second molecule are independently detectable. Presence of the rough-type *mycobacterium* is signaled by presence of the first molecule on the surface and presence of the smooth-type *mycobacterium* is signaled by presence of the second molecule on the surface.

A fourth embodiment is an assay (e.g., a lateral flow-type assay) for detecting a rough-type *mycobacterium* and a smooth-type *mycobacterium* in a sample, wherein the *mycobacterium* is *Mycobacterium tuberculosis* or *Mycobacterium bovis*. The assay comprises a sample zone, a conjugate zone and a test zone. The conjugate zone includes a first molecule that selectively binds to the rough-type *mycobacterium* or binds to a molecule preferentially secreted by the rough-type *mycobacterium* and a second molecule that selectively binds to the smooth-type *mycobacterium* or binds to a molecule preferentially secreted by the smooth-type *mycobacterium*. The test zone includes a third molecule immobilized in the test zone that binds to the *mycobacterium* or the molecule preferentially secreted by the rough-type *mycobacterium* and the molecule preferentially secreted by the smooth-type *mycobacterium*. The first and second molecules are independently detectable by optical microscopy. Presence of the rough-type *mycobacterium* is signaled by detection of the first molecule in the test zone, and presence of the smooth-type *mycobacterium* is signaled by detection of the second molecule in the test zone.

A fifth embodiment is an assay (e.g., a lateral flow-type assay) for detecting a rough-type *mycobacterium* and a smooth-type *mycobacterium* in a sample, wherein the *mycobacterium* is *Mycobacterium tuberculosis* or *Mycobacterium bovis*. The assay comprises a sample zone, a conjugate zone, a first test zone and a second test zone. The conjugate zone includes a detectable molecule that binds to the *mycobacterium* or a molecule preferentially secreted by the rough-type *mycobacterium* and a molecule preferentially secreted by the smooth-type *mycobacterium*. The first test zone includes a first molecule immobilized in the first test zone that selectively binds to the rough-type *mycobacterium* or the molecule preferentially secreted by the rough-type *mycobacterium*. The second test zone includes a second molecule immobilized in the second test zone that selectively binds to the smooth-type *mycobacterium* or the molecule preferentially secreted by the smooth-type *mycobacterium*. Presence of the rough-type *mycobacterium* is signaled by detection of the detectable protein in the first test zone, and presence of the smooth-type *mycobacterium* is signaled by detection of the detectable protein in the second test zone.

A sixth embodiment is an assay for detecting a rough-type *mycobacterium* and a smooth-type *mycobacterium* in a subject from whom a sample is obtained, wherein the *mycobacterium* is *Mycobacterium tuberculosis* or *Mycobacterium bovis*. The assay comprises a first molecule from the rough-type *mycobacterium* that induces a cytokine, wherein the cytokine induced by the first molecule is capable of contact with a first surface; a second molecule from the smooth-type *mycobacterium* that induces the cytokine, wherein the cytokine induced by the second molecule is capable of contact with a second surface; a molecule immobilized on the first surface and the second surface that binds to the cytokine; and a detectable molecule that binds to the cytokine. The first and second surfaces are independently detectable. Presence of the rough-type *mycobacterium* is signaled by presence of the detectable molecule on the first surface, and presence of the smooth-type *mycobacterium* is signaled by presence of the detectable molecule on the second surface.

A seventh embodiment is a method for detecting a rough-type *mycobacterium* and a smooth-type *mycobacterium* in a sample, wherein the *mycobacterium* is *Mycobacterium tuberculosis* or *Mycobacterium bovis*. The method comprises providing a sample and independently detecting the rough-type *mycobacterium* and the smooth-type *mycobacterium* in the sample, thereby detecting the rough-type *mycobacterium* and the smooth-type *mycobacterium* in the sample.

An eighth embodiment is a method for detecting tuberculosis infection. The method comprises providing a sample (e.g., a sample potentially infected with tuberculosis or suspected of tuberculosis infection) and independently detecting rough-type *Mycobacterium tuberculosis* and smooth-type *Mycobacterium tuberculosis* in the sample. Active tuberculosis infection is indicated by presence of rough-type *Mycobacterium tuberculosis* and presence of smooth-type *Mycobacterium tuberculosis* in the sample. Latent tuberculosis infection is indicated by presence of rough-type *Mycobacterium tuberculosis* and absence of smooth-type *Mycobacterium tuberculosis* in the sample.

The assays and methods described herein can be used in immunohistochemistry (IHC) microscopic examination of sputum smear and replace acid-fast staining protocols for the diagnosis of TB due to their increased sensitivity and specificity and lack of cross-reactivity with nontuberculous mycobacteria (NTM). It is hypothesized that R-type phase variants must convert from R-type to S-type during reactivation, and must convert from S-type to R-type during aerated growth in lung cavities. Therefore, the assays and methods described herein may enable detection of the reactivation of latent TB infection and the early phase of cavity formation post-reactivation, which could, in turn, enable diagnosis of TB before the disease becomes active.

BRIEF DESCRIPTION OF THE DRAWINGS

The foregoing will be apparent from the following more particular description of example embodiments of the invention, as illustrated in the accompanying drawings.

FIG. 2A shows H37Rv single cell/small aggregate preparations spread on 7H10 Dubos Oleic Albumin Complex (OADC) agar.

FIG. 2B shows $mc^24002$ single cell/small aggregate preparations spread on 7H10 OADC agar.

FIG. 2C shows single cell/small aggregate preparations of $mc^24019$ spread on 7H10 OADC agar. Complementation of $mc^24002$ with RD1 sequence led to all S morphotype colonies (RD1 complementation was as described in Hsu 2003 with cosmid 2F9 (Pym 2002).

FIG. 2D is a Southern analysis of S and R morphotype colonies from FIG. 2B and shows that both S and R morphotypes harbor the ΔRD1, but not wild type RD1 allele.

FIG. 2E shows a single colony of S morphotype of either H37Rv or $mc^24002$.

FIG. 2F shows a single colony of $mc^24002$ exhibiting the R morphotype at 4 weeks.

FIG. 2G shows a single colony of $mc^24002$ exhibiting the R morphotype at 8 weeks.

DETAILED DESCRIPTION OF THE INVENTION

Figure 1A:
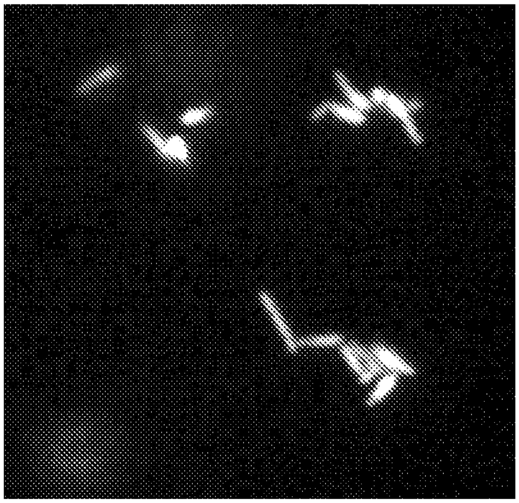
FIG. 1A is an image taken on a fluorescence microscope of $mc^2155$ (*M. smegmatis*) liquid culture before passing through a 5-μm filter.

A description of example embodiments of the invention follows.

Assays

A first embodiment is an assay for detecting a rough-type *mycobacterium* and a smooth-type *mycobacterium* in a sample, wherein the *mycobacterium* is *Mycobacterium tuberculosis* or *Mycobacterium bovis*. The assay comprises a first molecule that selectively binds to the rough-type *mycobacterium* or binds to a molecule preferentially secreted by the rough-type *mycobacterium* and a second molecule that selectively binds to the smooth-type *mycobacterium* or binds to a molecule preferentially secreted by the smooth-type *mycobacterium*. The first molecule and the second molecule are independently detectable.

"*Mycobacterium tuberculosis,*" "*M. tuberculosis*" and "Mtb" are used interchangeably herein and refer to both wild-type and recombinant strains of *Mycobacterium tuberculosis*, as well as derivatives and attenuated versions thereof. For example, "*Mycobacterium tuberculosis,*" "*M. tuberculosis*" and "Mtb" include the Mtb strains listed in Table 1 and described in the corresponding references cited in Table 1.

*Mycobacterium tuberculosis* is the causative agent of TB in humans and is spread through the air from one person to another. Accurate and timely detection of Mtb infection enables diagnosis of TB, treatment of patients with TB and prevention of spread of TB. Accordingly, in some aspects, the *mycobacterium* is Mtb. In further aspects, the *mycobacterium* is Mtb and the assay is an assay for detecting tuberculosis infection (e.g., active tuberculosis infection, latent tuberculosis infection) in a sample (e.g., a sample derived from a human). In yet further aspects, the *mycobacterium* is Mtb and the assay is an assay for diagnosing tuberculosis infection in a subject (e.g., a human).

"Active tuberculosis infection" refers to tuberculosis associated with symptoms, sometimes referred to as tuberculosis disease. In some aspects, active tuberculosis infection is indicated by presence of rough-type *Mycobacterium tuberculosis* and presence of smooth-type *Mycobacterium tuberculosis* in a sample.

"Latent tuberculosis infection" refers to tuberculosis infection not associated with symptoms. Latent tuberculosis can occur in subjects who have previously had the disease and/or been cured of the disease. The infection can live dormant in the lungs for many years without causing symptoms. In some aspects, latent tuberculosis infection is indicated by presence of rough-type *Mycobacterium tuberculosis* and absence or substantial absence of smooth-type *Mycobacterium tuberculosis* in a sample.

"*Mycobacterium bovis*" and "*M. bovis*" are used interchangeably herein and refer to both wild-type and recombinant strains of *Mycobacterium bovis*, as well as derivatives and attenuated versions thereof. For example, "*Mycobacterium bovis*" and "*M. bovis*" include the *M. bovis* strains listed in Table 1 and described in the corresponding references cited in Table 1.

*Mycobacterium bovis* is the causative agent of TB in cattle and other animals, and can also cause TB in humans. Accurate and timely detection of *M. bovis* infection enables diagnosis of TB, treatment of subjects or patients with TB and prevention of spread of TB. Accordingly, in some aspects, the *mycobacterium* is *M. bovis*. In further aspects, the *mycobacterium* is *M. bovis* and the assay is an assay for detecting tuberculosis infection (e.g., active tuberculosis infection, latent tuberculosis infection) in a sample (e.g., a sample derived from a human, a bovine or other animal). In yet further aspects, the *mycobacterium* is *M. bovis* and the assay is an assay for diagnosing tuberculosis infection in a subject (e.g., a human, a bovine or other animal).

As used herein, the singular forms "a," "an" and "the" include plural referents unless the context clearly dictates otherwise. Thus, for example, reference to "a protein" can include a plurality of proteins. Further, the plurality can comprise more than one of the same protein or a plurality of different proteins.

As used herein, "detecting" means identifying the presence (or absence) of. Accordingly, detecting a rough-type *mycobacterium* and a smooth-type *mycobacterium* in a sample includes determining whether or not the rough-type *mycobacterium* is present in (or absent from) the sample and whether or not the smooth-type *mycobacterium* is present in (or absent from) the sample. Detection of the rough-type *mycobacterium* and the smooth-type *mycobacterium* may occur concurrently or detection of the rough-type *mycobacterium* or smooth-type *mycobacterium* may precede detection of the smooth-type *mycobacterium* or rough-type *mycobacterium*, respectively.

Detecting infection (e.g., TB infection) in a sample includes determining whether or not the bacterium responsible for the infection (e.g., *Mycobacterium tuberculosis*) is present in the sample. When detecting infection (e.g., active TB infection, latent TB infection) in a sample includes detecting a rough-type *mycobacterium* responsible for the infection (e.g., *Mycobacterium tuberculosis*) in the sample and detecting a smooth-type *mycobacterium* responsible for the infection (e.g., *Mycobacterium tuberculosis*) in the sample, detection of the responsible *mycobacterium* and detection of the R or S or R and S types of the *mycobacterium* may occur concurrently. Detection of the responsible *mycobacterium* may also precede detection of the R or S or R and S types of the *mycobacterium*, for example, if detection of the responsible *mycobacterium* occurs during a prior step, such as an initial screen.

"Molecule," as used herein, refers to a chemical entity that can participate in a binding interaction with another molecule or a chemical moiety expressed by a bacterium or other cell. Examples of molecules include proteins (e.g., lectins; antibodies, especially monoclonal antibodies; cytokines, such as interferons, especially interferon gamma), peptides and small, organic molecules (e.g., organic compounds having a molecular weight of less than about 900 Daltons, less than about 750 Daltons, less than about 600 Daltons or less than about 500 Daltons). Small, organic molecules include, for example, lipids, monosaccharides, second messengers and other natural products and metabolites, as well as many drugs.

In some aspects, the first molecule is a protein, for example, an antibody, in particular, a monoclonal antibody. In other aspects, the second molecule is a protein, for example, an antibody, in particular, a monoclonal antibody. In some aspects, the first molecule is a protein, for example, an antibody, in particular, a monoclonal antibody and the second molecule is a protein, for example, an antibody, in particular, a monoclonal antibody. Other types of antibodies useful in certain aspects of the assays and methods described herein include recombinant antibodies, single-chain antibodies, synthetic antibodies, antibody fragments and type-specific polyclonal antibodies from any source(s) or animal(s).

Detection of molecules can be accomplished in a variety of ways generally known to those of skill in the art. For example, proteins are commonly detected through the use of molecular labels, such as biotin, an enzyme reporter, a fluorophore or a radioactive isotope, that are covalently attached to the protein. Such covalently-labelled proteins can be detected by colorimetric, fluorescent or chemiluminescent techniques or means for detecting radioactivity, such as scintillation counting. Proteins can also be detected using means that do not rely on covalent modification of the protein, such as by exploiting an antibody-antigen interaction. Accordingly, detection can be direct, as when a protein is covalently labelled with a fluorophore that is directly detected by fluorescence microscopy, or indirect, as when an unlabeled protein is detected via a conjugated antibody. Lipid molecules on the surface of *M. tuberculosis* can be stained with chemical dyes such as carbol fuchsin, as in acid-fast staining, or with auramine-O or auramine-rhodamine for fluorescence microscopy. Many of the same techniques can be exploited to detect peptides and small, organic molecules, as is known in the art. A "detectable molecule" is a molecule that is capable of being detected, for example, by one of the commonly employed methods listed above.

"Independently detectable," as used herein with respect to a first molecule that selectively binds to a rough-type *mycobacterium* or binds to a molecule preferentially secreted by the rough-type *mycobacterium* and a second molecule that selectively binds to a smooth-type *mycobacterium* or binds to a molecule preferentially secreted by the smooth-type *mycobacterium*, means the two molecules can be detected separately from one another. For example, a first protein labelled with a first fluorophore with a first emission spectrum and a second protein labelled with a second fluorophore with a second emission spectrum different from the emission spectrum of the first fluorophore can be independently detectable. Such pairings include, for example, a BODIPY dye and a Qdot nanocrystal or green fluorescent protein and red fluorescent protein. A first protein detectable by a means for detecting radioactivity and a second protein detectable by fluorescence microscopy are also independently detectable. Independently detectable proteins are typically detected sequentially, but may also be detected concurrently, as technology allows. It is expected that by detecting the presence of both rough and smooth types of a *mycobacterium*, the assays and methods described herein will provide superior specificity and fewer false results than existing methods for detecting and diagnosing TB.

Often, a sample in which an infection described herein is to be detected is derived from a subject and, in preferred aspects, the sample is derived from a human. A sample can be blood, sputum, phlegm, urine or stool, for example, derived from a subject, in particular, a human (e.g., a human suspected of tuberculosis infection). Samples also include aerosols, such as dust.

As used herein, "subject" refers to an animal. "Subject" includes birds and mammals (e.g., humans, non-human primates, cows, sheep, goats, horses, dogs, cats, rabbits, guinea pigs, rats, mice, etc.). In preferred aspects, the subject is a human.

Colony morphology is often described and in some cases its variation is amenable to genetic analysis. In the case of *M. tuberculosis*, observations of changes in colony morphology began almost from the first description of this organism as the causative agent of tuberculosis and continue into the recent literature. Although the shape of each bacterial colony is unique in detail, colony morphology variants are well known to microbiologists by classical descriptions including "rough" and "smooth."

As used herein, "rough," "rough-type," "raised," "R" and "R-type" are used interchangeably to refer to a variant of a reference *mycobacterium* (e.g., Mtb) whose surface, when grown on a plate is characterized visually by an irregular shape in both two and three dimensions. When grown on an agar plate, a colony of rough-type mycobacteria is typically raised from the surface on which it is growing. See FIG. 7.

As used herein, "smooth," "smooth-type," "spread," "S" and "S-type" are used interchangeably to refer to a variant of a reference *mycobacterium* (e.g., Mtb) whose surface, when grown on a plate, is characterized visually by being round in two dimensions and dome-shaped in three dimensions and lacking indentations or sharp angles. The surface of a colony of smooth-type mycobacteria grown on an agar plate can be described as continuous and shining. See FIG. 7.

"Phase variation" is heritable but semi-stable and reversible phenotypic variation. All clonal populations of bacteria, if they are sufficiently large, contain genotypic and phenotypic variants. In phase variation, when a single cell of one variant type is isolated and regrown, the new population contains variants that include the original type. Authors of older literature did not make distinctions of altered gene expression, mutation, and phase variation in their studies of morphotypes. These features, now understood to be conceptually distinct but related, were grouped together under the heading of "microbial dissociation." For this reason, the older literature while valid as observation can only be relied on as an indication that phenotypic alterations in colony morphology occur but not for the analysis of its heritability. The work reported herein shows that mycobacterial colony morphotypes display the formal genetic characteristics of phase variation. Accordingly, the usage of "rough" and "smooth" herein should not be confused with usage of the terms "rough" and "smooth" by classical microbiologists. As used herein, "rough" and "raised" and "smooth" and "spread" should be understood to incorporate the understanding that mycobacteria described herein exhibit phase variation.

Visual observation has led to the hypothesis that rough- and smooth-type colonies of the mycobacteria described herein exhibit differential expression of certain proteins, lipids polysaccharides, and/or molecules comprising combinations of the aforementioned molecules (e.g., glycoproteins, glycolipids, lipoproteins). Accordingly, rough and smooth types of the mycobacteria described herein can also be characterized on the basis of differential expression of certain lipids and/or polysaccharides.

Rough and smooth mycobacteria disclosed herein can also be characterized by differential gene expression. Microarray analysis of R- and S-type *M. tuberculosis* detected several genes differentially regulated by the two types. Table 2 lists genes up-regulated by at least 2 fold in the R-type colonies of H37Rv (*M. tuberculosis* ΔRD1 ΔpanCD), compared to S-type, and Table 3 lists genes up-regulated by at least 2 fold in the S-type colonies of H37Rv (*M. tuberculosis* ΔRD1 ΔpanCD), compared to R-type.

It is expected that the observed genetic differences result in differential expression of the proteins encoded by the identified genes. Thus, rough and smooth mycobacteria described herein can also be characterized on the basis of differential protein expression. The proteins encoded by the *M. tuberculosis* genes listed in Tables 2 and 3 are also identified in Tables 2 and 3, respectively.

In some aspects, the first molecule selectively binds to the rough-type *mycobacterium*. In other aspects, the second molecule selectively binds to the smooth-type *mycobacterium*. In some aspects, the first molecule selectively binds to the rough-type *mycobacterium* and the second molecule selectively binds to the smooth-type *mycobacterium*.

A molecule "binds to" a *mycobacterium* if the dissociation constant ($K_d$) of the interaction between the two species is less than about 10 μM, less than about 1 μM, or less than about 100 nM. It will be understood that when a molecule "binds to" a *mycobacterium* (e.g., a rough-type *mycobacterium*, a smooth-type *mycobacterium*), the molecule is participating in a binding interaction with a chemical moiety expressed by the *mycobacterium*, such as a protein, lipid or polysaccharide. The binding interaction can be covalent or non-covalent.

A molecule "selectively binds to" or "is selective for" an R-type *mycobacterium* if the molecule binds to the R-type *mycobacterium* to a greater extent than to the corresponding S-type *mycobacterium*. Conversely, a molecule "selectively binds to" or "is selective for" an S-type *mycobacterium* if the molecule binds to the S-type *mycobacterium* to a greater extent that to the corresponding R-type *mycobacterium*. It is preferred that the molecule bind to R-type *mycobacterium* or S-type *mycobacterium* at least about two-fold, at least about three-fold, at least about four-fold, at least about five-fold, at least about ten-fold, and most preferably at least about fifty-fold more strongly than the corresponding S-type *mycobacterium* or R-type *mycobacterium*, respectively. Most preferably, a molecule that is selective for R-type mycobacteria will not bind to the corresponding S-type mycobacteria to any measurable or detectable degree, and a molecule that is selective for S-type mycobacteria will not bind to the corresponding R-type mycobacteria to any measurable or detectable degree.

Binding can be signaled by detection of a signal produced by a molecule in accordance with the detection techniques discussed herein. In some aspects, the signal is an optical signal, such as luminescence, fluorescence or absorbance. Therefore, the signal produced by the molecule can be measured using optical methods, for example, luminescence, absorbance or fluorescence spectroscopy. Alternatively or in addition, means for detecting radioactivity, such as scintillation counting, can be used to detect binding.

In some aspects, the first molecule binds to a molecule preferentially secreted by the rough-type *mycobacterium*. In other aspects, the second molecule binds to a molecule preferentially secreted by the smooth-type *mycobacterium*. In some aspects, the first molecule binds to a molecule preferentially secreted by the rough-type *mycobacterium* and the second molecule binds to a molecule preferentially secreted by the smooth-type *mycobacterium*.

A molecule is "preferentially secreted by" an R-type *mycobacterium* if the molecule is secreted by the R-type *mycobacterium* to a greater extent than by the corresponding S-type *mycobacterium*. Conversely, a molecule is "preferentially secreted by" an S-type *mycobacterium* if the molecule is secreted by the S-type *mycobacterium* to a greater extent that by the corresponding R-type *mycobacterium*. It is preferred that secretion of the molecule by R-type *mycobacterium* or S-type *mycobacterium* be at least about two-fold, at least about three-fold, at least about four-fold, at least about five-fold, at least about ten-fold, and most preferably at least about fifty-fold greater than secretion of the molecule by the corresponding S-type *mycobacterium* or R-type *mycobacterium*, respectively. Most preferably, a molecule that is preferentially secreted by R-type mycobacteria will not be secreted by the corresponding S-type mycobacteria to any measurable or detectable degree, and a molecule that is preferentially secreted by S-type mycobacteria will not be secreted by the corresponding R-type mycobacteria to any measurable or detectable degree.

In some aspects, the first molecule binds to a protein, lipid or polysaccharide preferentially expressed by the rough-type *mycobacterium*, for example, a cell surface protein, lipid or polysaccharide. In other aspects, the second molecule binds to a protein, lipid or polysaccharide preferentially expressed by the smooth-type *mycobacterium*, for example, a cell surface protein, lipid or polysaccharide. In some aspects, the first molecule binds to a protein, lipid or polysaccharide preferentially expressed by the rough-type *mycobacterium*, for example, a cell surface protein, lipid or polysaccharide, and the second molecule binds to a protein, lipid or polysaccharide preferentially expressed by the smooth-type *mycobacterium*, for example, a cell surface protein, lipid or polysaccharide.

As used herein, a molecule or protein, lipid or polysaccharide is "preferentially expressed" by an R-type *mycobacterium* if the molecule or protein, lipid or polysaccharide is expressed to a greater extent than the molecule or protein, lipid or polysaccharide is expressed by the corresponding S-type *mycobacterium*. Conversely, a molecule or protein, lipid or polysaccharide is "preferentially expressed" by an S-type *mycobacterium* if the molecule or protein, lipid or polysaccharide is expressed to a greater extent than the molecule or protein, lipid or polysaccharide is expressed by the corresponding R-type *mycobacterium*. It is preferred that the expression of the molecule or protein, lipid or polysaccharide preferentially expressed by the R-type *mycobacterium* or S-type *mycobacterium* is at least about two-fold, at least about three-fold, at least about four-fold, at least about five-fold, at least about ten-fold, and most preferably at least about fifty-fold greater than the expression of the molecule or protein, lipid or polysaccharide preferentially expressed by the S-type *mycobacterium* or R-type *mycobacterium*, respectively. Most preferably, a molecule or protein, lipid or polysaccharide that is preferentially expressed by R-type mycobacteria will not be expressed by the corresponding S-type mycobacteria to any measurable or detectable degree, and a molecule or protein, lipid or polysaccharide that is preferentially expressed by S-type mycobacteria will not be expressed by the corresponding R-type mycobacteria to any measurable or detectable degree. Expression of a molecule or protein, lipid or polysaccharide can be detected and measured using methods known to those of skill in the art, for example, thin-layer chromatography, protein gel electrophoresis, Western blot, mass spectrometry.

As previously stated, visual observation has led to the hypothesis that rough and smooth types of the mycobacteria described herein exhibit differential expression of certain lipids and/or polysaccharides. Lipids preferentially expressed by the R-type mycobacteria described herein include phthiocerol dimycocerosate, a sterol, a sulfolipid, a glycolipid (e.g., trehalose dimycolate), a lipoligosaccharide or a phospholipid (e.g., phosphatidylinositol mannoside).

Microarray analysis has also detected differentially expressed genes in the mycobacteria described herein. Genes preferentially expressed by the R-type mycobacteria described herein (e.g., *M. tuberculosis*) include TB31.7, fdXA, hrp1, acg, groES, groE2, narX, icl1, sigE, sigB, hspX, mbtC, tgsl, lat and pfkB. Genes preferentially expressed by the S-type mycobacteria described herein (e.g., *M. tuberculosis*) include moeA1, pe13, pepR, leuC, choD, aao, fabG, tsnR, leuD, pe25 and ispD.

Proteins preferentially expressed by the R-type mycobacteria described herein (e.g., *M. tuberculosis*) include universal stress protein family protein TB31.7, ferredoxin (FdxA), hypoxic response protein 1 (Hrp1), chaperonin GroES, chaperonin 2 (GroEL2), nitrate reductase (NarX), isocitrate lyase (Icll), RNA polymerase sigma factor (sigE), RNA polymerase sigma factor (sigB), heat shock protein (HspX), polyketide synthetase MbtC, triacylglycerol synthase (Tgsl), L-lysine-epsilon aminotransferase (Lat) and 6-phosphofructokinase (pfkB). Proteins preferentially expressed by the S-type mycobacteria described herein (e.g., *M. tuberculosis*) include molybdopterin biosynthesis protein (MoeA1), PE family protein PE13, zinc protease (PepR), 3-isopropylmalate dehydratase (LeuC), cholesterol oxidase (ChoD), D-amino acid oxidase (Aao), 3-oxoacyl-[acyl-carrier protein] reductase (FabG4), pyridoxamine 5'-phosphate oxidase (PNP/PMP oxidase) 23S rRNA methyltransferase (tsnR), 3-isopropylmalate dehydratase (LeuD), PE family protein PE25 and 4-diphosphocytidyl-2C-methyl-D-erythritol synthase IspD (MEP cytidyltransferase).

A second embodiment is an assay for detecting tuberculosis infection in a sample. The assay comprises a first molecule that selectively binds to rough-type *Mycobacterium tuberculosis* or binds to a molecule preferentially secreted by rough-type *Mycobacterium tuberculosis* and a second molecule that selectively binds to smooth-type *Mycobacterium tuberculosis* or binds to a molecule preferentially secreted by smooth-type *Mycobacterium tuberculosis*. The first molecule and the second molecule are independently detectable. Active tuberculosis infection is indicated by presence of rough-type *Mycobacterium tuberculosis*, as signaled by detection of the first molecule, and presence of smooth-type *Mycobacterium tuberculosis*, as signaled by detection of the second molecule. Latent tuberculosis infection is indicated by presence of rough-type

*Mycobacterium tuberculosis*, as signaled by detection of the first molecule, and absence of smooth-type *Mycobacterium tuberculosis*, as signaled by detection of the second molecule. Variations of the assay are as described with respect to the first embodiment or any aspect thereof.

In some aspects, the assay is an assay for detecting active tuberculosis infection in a sample and active tuberculosis infection is indicated by presence of rough-type *Mycobacterium tuberculosis*, as signaled by detection of the first molecule, and presence of smooth-type *Mycobacterium tuberculosis*, as signaled by detection of the second molecule. In some aspects, the assay is an assay for detecting latent tuberculosis infection in a sample and latent tuberculosis infection is indicated by presence of rough-type *Mycobacterium tuberculosis*, as signaled by detection of the first molecule, and absence of smooth-type *Mycobacterium tuberculosis*, as signaled by detection of the second molecule.

A third embodiment is a sputum-smear assay for detecting a rough-type *mycobacterium* and a smooth-type *mycobacterium* in a sample, wherein the *mycobacterium* is *Mycobacterium tuberculosis* or *Mycobacterium bovis* and is immobilized on a surface (e.g., a glass slide). The assay comprises a first molecule that selectively binds to the rough-type *mycobacterium* and a second molecule that selectively binds to the smooth-type *mycobacterium*. The first molecule and the second molecule are independently detectable. Presence of the rough-type *mycobacterium* is signaled by presence of the first molecule on the surface and presence of the smooth-type *mycobacterium* is signaled by presence of the second molecule on the surface. Variations of the assay are as described with respect to the first embodiment or any aspect thereof.

As used herein, "immobilized" means fixed in place. Immobilization can be covalent, as when a molecule, such as a protein, is covalently attached to a surface, or non-covalent, as when a cell or cell culture is smeared on a surface, such as a glass slide, or a protein functionalized with magnetic beads is held in place by a magnet. When a molecule, cell or sample is immobilized, it should typically remain in place for the duration of the assay, even when subjected to, for example, conventional rinsing steps necessary to conduct the assays described herein.

The assays described herein can conveniently be employed in lateral flow devices. Thus, a fourth embodiment is an assay (e.g., a lateral flow-type assay) for detecting a rough-type *mycobacterium* and a smooth-type *mycobacterium* in a sample, wherein the *mycobacterium* is *Mycobacterium tuberculosis* or *Mycobacterium bovis*. The assay comprises a sample zone, a conjugate zone and a test zone. The conjugate zone includes a first molecule that selectively binds to the rough-type *mycobacterium* or binds to a molecule preferentially secreted by the rough-type *mycobacterium* and a second molecule that selectively binds to the smooth-type *mycobacterium* or binds to a molecule preferentially secreted by the smooth-type *mycobacterium*. The test zone includes a third molecule immobilized in the test zone that binds to the *mycobacterium* or the molecule preferentially secreted by the rough-type *mycobacterium* and the molecule preferentially secreted by the smooth-type *mycobacterium*. The first and second molecules are independently detectable by optical microscopy. Presence of the rough-type *mycobacterium* is signaled by detection of the first molecule in the test zone, and presence of the smooth-type *mycobacterium* is signaled by detection of the second molecule in the test zone. Variations of the assay are as described with respect to the first embodiment or any aspect thereof.

In use, a sample is applied to the sample zone of a lateral flow device according to the fifth embodiment, and the sample flows from the sample zone onto or through the conjugate zone, where the sample is exposed to the first and second molecules under conditions suitable to form a first molecule-rough *mycobacterium* conjugate and a second molecule-smooth *mycobacterium* conjugate or a first molecule-secreted rough *mycobacterium* molecule conjugate and a second molecule-secreted smooth *mycobacterium* molecule conjugate. From the conjugate zone, the sample as well as any conjugates formed flow onto the test zone, where the conjugates are captured by the third molecule to form a first molecule-rough *mycobacterium*-third molecule conjugate and a second molecule-smooth *mycobacterium*-third molecule conjugate or a first molecule-secreted rough *mycobacterium* molecule-third molecule conjugate and a second molecule-secreted smooth *mycobacterium* molecule-third molecule conjugate. The test zone provides a convenient location to detect the first and second molecules, thereby enabling detection of rough and smooth mycobacteria or detection of infection, as signaled by presence of rough and smooth mycobacteria.

A fifth embodiment is an assay (e.g., a lateral flow-type assay) for detecting a rough-type *mycobacterium* and a smooth-type *mycobacterium* in a sample, wherein the *mycobacterium* is *Mycobacterium tuberculosis* or *Mycobacterium bovis*. The assay comprises a sample zone, a conjugate zone, a first test zone and a second test zone. The conjugate zone includes a detectable molecule that binds to the *mycobacterium* or a molecule preferentially secreted by the rough-type *mycobacterium* and a molecule preferentially secreted by the smooth-type *mycobacterium*. The first test zone includes a first molecule immobilized in the first test zone that selectively binds to the rough-type *mycobacterium* or the molecule preferentially secreted by the rough-type *mycobacterium*. The second test zone includes a second molecule immobilized in the second test zone that selectively binds to the smooth-type *mycobacterium* or the molecule preferentially secreted by the smooth-type *mycobacterium*. Presence of the rough-type *mycobacterium* is signaled by detection of the detectable protein in the first test zone, and presence of the smooth-type *mycobacterium* is signaled by detection of the detectable protein in the second test zone. Variations of the assay are as described with respect to the first embodiment or any aspect thereof.

In use, a sample is applied to the sample zone of a lateral flow device according to the fifth embodiment, and the sample flows from the sample zone onto or through a conjugate zone, where the sample is exposed to the detectable molecule under conditions suitable to form a detectable molecule-*mycobacterium* conjugate or a detectable molecule-secreted rough *mycobacterium* molecule conjugate and a detectable molecule-secreted smooth *mycobacterium* molecule conjugate. From the conjugate zone, the sample as well as any conjugates formed flow onto the test zones under conditions suitable to form a detectable molecule-rough *mycobacterium*-first molecule conjugate or a detectable molecule-secreted rough *mycobacterium* molecule-first molecule conjugate, and a detectable molecule-smooth *mycobacterium*-second molecule conjugate or a detectable molecule-secreted smooth *mycobacterium* molecule-second molecule conjugate. The first test zone captures detectable molecule-rough *mycobacterium* conjugates or detectable molecule-secreted rough *mycobacterium* molecule conjugates to form a detectable molecule-rough *mycobacterium*-first molecule conjugate or a detectable molecule-secreted rough *mycobacterium* molecule-first molecule conjugate. The second test zone captures detectable molecule-smooth *mycobacterium* conjugates or detectable molecule-secreted smooth *mycobacterium* molecule conjugates to form a detectable molecule-smooth *mycobacterium*-second molecule conjugate or a detectable molecule-secreted smooth *mycobacterium* molecule-second molecule conjugate. The test zones provide a convenient location to detect the detectable molecule, thereby enabling detection of rough and smooth mycobacteria or detection of infection, as signaled by presence of rough and smooth mycobacteria.

A sixth embodiment is an assay for detecting a rough-type *mycobacterium* and a smooth-type *mycobacterium* in a subject from whom a sample is obtained, wherein the *mycobacterium* is *Mycobacterium tuberculosis* or *Mycobacterium bovis*. The assay comprises a first molecule (e.g., antigen, such as a protein, lipid or polysaccharide, or a combination of any of the foregoing molecules) from the rough-type *mycobacterium* that induces a cytokine (e.g., a cytokine released from a T-cell lymphocyte, such as interferon gamma), wherein the cytokine induced by the first molecule is capable of contact with a first surface; a second molecule (e.g., antigen, such as a protein, lipid or polysaccharide, or a combination of any of the foregoing molecules) from the smooth-type *mycobacterium* that induces the cytokine, wherein the cytokine induced by the second molecule is capable of contact with a second surface; a molecule immobilized on the first surface and the second surface that binds to the cytokine; and a detectable molecule that binds to the cytokine. The first and second surfaces are independently detectable. Presence of the rough-type *mycobacterium* is signaled by presence of the detectable molecule on the first surface, and presence of the smooth-type *mycobacterium* is signaled by presence of the detectable molecule on the second surface. Variations of the assay are as described with respect to the first embodiment or any aspect thereof. For example, the antigenic protein, lipid or polysaccharide from the rough-type *mycobacterium* or the smooth-type *mycobacterium* include those discussed herein with respect to the assays or methods.

Representative assays of this type are known in the art as interferon gamma release assays and include both enzyme-linked immunospot (ELISPOT) assays and enzyme-linked immunosorbent (ELISA) assays, which can be used to detect TB in blood samples.

"Independently detectable," as used herein with respect to a surface, means the two surfaces can be detected separately from one another. For example, a first surface can be spatially separated from a second surface, as are two wells of a 96-well plate.

Methods

A seventh embodiment is a method for detecting a rough-type *mycobacterium* and a smooth-type *mycobacterium* in a sample, wherein the *mycobacterium* is *Mycobacterium tuberculosis* or *Mycobacterium bovis*. The method comprises providing a sample and independently detecting the rough-type *mycobacterium* and the smooth-type *mycobacterium* in the sample, thereby detecting the rough-type *mycobacterium* and the smooth-type *mycobacterium* in the sample.

An eighth embodiment is a method for detecting tuberculosis infection (e.g., active tuberculosis infection, latent tuberculosis infection). The method comprises providing a sample (e.g., a sample potentially infected with tuberculosis or suspected of tuberculosis infection, for example, a sample derived from a human) and independently detecting rough-type *Mycobacterium tuberculosis* and smooth-type *Mycobacterium tuberculosis* in the sample. Active tuberculosis infection is indicated by presence of rough-type *Mycobacterium tuberculosis* and presence of smooth-type *Mycobacterium tuberculosis* in the sample. Latent tuberculosis infection is indicated by presence of rough-type *Mycobacterium tuberculosis* and absence or substantial absence of smooth-type *Mycobacterium tuberculosis* in the sample.

In some aspects, the method is a method for detecting active tuberculosis infection, which is indicated by presence of rough-type *Mycobacterium tuberculosis* and presence of smooth-type *Mycobacterium tuberculosis* in the sample. In some aspect, the method is a method for detecting latent tuberculosis infection, which is indicated by presence of rough-type *Mycobacterium tuberculosis* and absence or substantial absence of smooth-type *Mycobacterium tuberculosis* in the sample.

Samples include those described above with respect to the assays.

In some aspects, the *mycobacterium* is Mtb. In further aspects, the *mycobacterium* is Mtb and the method is a method for detecting tuberculosis infection (e.g., active tuberculosis infection, latent tuberculosis infection) in a sample (e.g., a sample derived from a human). In yet further aspects, the *mycobacterium* is Mtb and the method is a method for diagnosing tuberculosis infection in a subject (e.g., a human).

In other aspects, the *mycobacterium* is *M. bovis*. In further aspects, the *mycobacterium* is *M. bovis* and the method is a method for detecting tuberculosis infection (e.g., active tuberculosis infection, latent tuberculosis infection) in a sample (e.g., a sample derived from a human). In yet further aspects, the *mycobacterium* is *M. bovis* and the method is a method for diagnosing tuberculosis infection in a subject (e.g., a human).

In some aspects, detecting the rough-type *mycobacterium* comprises visually inspecting the surface of a colony of the *mycobacterium*, wherein a colony of *mycobacterium* whose surface is irregular in shape in both two and three dimensions is rough-type. In other aspects, detecting the smooth-type *mycobacterium* comprises visually inspecting the surface of a colony of the *mycobacterium*, wherein a colony of *mycobacterium* whose surface is round in two dimensions and dome-shaped in three dimensions and lacks indentations or sharp angles is smooth-type. In some aspects, detecting the rough-type *mycobacterium* comprises visually inspecting the surface of a colony of the *mycobacterium*, wherein a colony of *mycobacterium* whose surface is irregular in shape in both two and three dimensions is rough-type and detecting the smooth-type *mycobacterium* comprises visually inspecting the surface of a colony of the *mycobacterium*, wherein a colony of *mycobacterium* whose surface is round in two dimensions and dome-shaped in three dimensions and lacks indentations or sharp angles is smooth-type.

Visual detection of the rough-type *mycobacterium* and the smooth-type *mycobacterium* has enabled the isolation of rough-type mycobacteria from smooth-type mycobacteria and smooth-type mycobacteria from rough-type mycobacteria. Thus, in some aspects, the methods further comprise isolating the rough-type *mycobacterium* (e.g., isolating the rough-type *mycobacterium* from the smooth-type *mycobacterium*). In other aspects the methods further comprise isolating the smooth-type *mycobacterium* (e.g., isolating the smooth-type *mycobacterium* from the rough-type *mycobacterium*). In some aspects, the methods further comprise isolating the rough-type *mycobacterium* (e.g., isolating the rough-type *mycobacterium* from the smooth-type *mycobacterium*) and isolating the smooth-type *mycobacterium* (e.g., isolating the smooth-type *mycobacterium* from the rough-type *mycobacterium*).

In some aspects, detecting the rough-type bacterium comprises detecting mRNA preferentially expressed by the rough-type *mycobacterium*. mRNA preferentially expressed by the rough-type *mycobacterium* (e.g., *M. tuberculosis*) includes mRNA transcribed from a gene selected from TB31.7, fdxA, hrp1, acg, groES, groE2, narX, icl1, sigE, sigB, hspX, mbtC, tgsl, lat and pfkB. In some aspects, the mRNA preferentially expressed by the rough-type *mycobacterium* is preferentially expressed by the rough-type *mycobacterium* compared to the smooth-type *mycobacterium* by a factor of at least about 2, at least about 3, at least about 4 or at least about 5. Table 2 lists specific genes implicated in a microarray analysis of R-type *M. tuberculosis*, as well as the factor by which their expression was increased in the rough type compared to the smooth type.

In some aspects, detecting the rough-type *mycobacterium* comprises detecting mRNA downregulated in the rough-type *mycobacterium* compared to the smooth-type *mycobacterium*. mRNA downregulated in the rough-type *mycobacterium* compared to the smooth-type *mycobacterium* includes mRNA transcribed from a gene selected from moeA1, pe13, pepR, leuC, choD, aao, fabG, tsnR, leuD, pe25 and ispD. In some aspects, the mRNA downregulated in the rough-type *mycobacterium* compared to the smooth-type *mycobacterium* is downregulated in the rough-type *mycobacterium* compared to the smooth-type *mycobacterium* by a factor of at least about 2, at least about 3, at least about 4 or at least about 5.

In some aspects, detecting the smooth-type *mycobacterium* comprises detecting mRNA preferentially expressed by the smooth-type *mycobacterium*. mRNA preferentially expressed by the smooth-type *mycobacterium* (e.g., *M. tuberculosis*) includes mRNA transcribed from a gene selected from moeA1, pe13, pepR, leuC, choD, aao, fabG, tsnR, leuD, pe25 and ispD. In some aspects, the mRNA preferentially expressed by the smooth-type *mycobacterium* is preferentially expressed in the smooth-type *mycobacterium* compared to the rough-type *mycobacterium* by a factor of at least about 2, at least about 3, at least about 4 or at least about 5. Table 3 lists specific genes implicated in a microarray analysis of S-type *M. tuberculosis*, as well as the factor by which their expression was increased in the smooth type compared to the rough type.

In some aspects, detecting the smooth-type *mycobacterium* comprises detecting mRNA downregulated in the smooth-type *mycobacterium* compared to the rough-type *mycobacterium*. mRNA downregulated in the smooth-type *mycobacterium* compared to the rough-type *mycobacterium* includes mRNA transcribed from a gene selected from TB31.7, fdxA, hrp1, acg, groES, groE2, narX, icl1, sigE, sigB, hspX, mbtC, tgsl, lat and pfkB. In some aspects, the mRNA downregulated in the smooth-type *mycobacterium* compared to the rough-type *mycobacterium* is downregulated in the smooth-type *mycobacterium* compared to the rough-type *mycobacterium* by a factor of at least about 2, at least about 3, at least about 4 or at least about 5.

In some aspects, detecting the rough-type bacterium comprises detecting mRNA preferentially expressed by the rough-type *mycobacterium* and detecting mRNA downregulated in the rough-type *mycobacterium* compared to the smooth-type *mycobacterium*. In some aspects, detecting the smooth-type *mycobacterium* comprises detecting mRNA preferentially expressed by the smooth-type *mycobacterium* and detecting mRNA downregulated in the smooth-type *mycobacterium* compared to the rough-type *mycobacterium*. Tables 2 and 3 list specific genes implicated in a microarray analysis of R- and S-type *M. tuberculosis*, as well as the factor by which their expression was increased or decreased in the smooth type compared to the rough type. Thus, in some aspects, detecting the rough-type bacterium comprises detecting mRNA preferentially expressed by the rough-type *mycobacterium* and detecting mRNA downregulated in the rough-type *mycobacterium* compared to the smooth-type *mycobacterium*, for example, wherein one or more mRNA (e.g., one, two, three, four, five, five or more or each of the mRNA listed in Tables 2 and 3) is preferentially expressed by or downregulated in the rough-type *mycobacterium* by the factor indicated in Table 2 or 3; and detecting the smooth-type *mycobacterium* comprises detecting mRNA preferentially expressed by the smooth-type *mycobacterium* and detecting mRNA downregulated in the smooth-type *mycobacterium* compared to the rough-type *mycobacterium*, for example, wherein the mRNA (e.g., one, two, three, four, five, five or more or each of the mRNA listed in Tables 2 and 3) is preferentially expressed by or downregulated in the smooth-type *mycobacterium* by the factor indicated in Table 2 or 3.

In some aspects, detecting the rough-type *mycobacterium* comprises detecting a protein, lipid or polysaccharide preferentially expressed by the rough-type *mycobacterium*. In a more particular aspect, detecting the rough-type *mycobacterium* comprises detecting a lipid preferentially expressed by the rough-type *mycobacterium*. In another particular aspect, detecting the rough-type *mycobacterium* comprises detecting a polysaccharide preferentially expressed by the rough-type *mycobacterium*. In yet another particular aspect, detecting the rough-type *mycobacterium* comprises detecting a protein preferentially expressed by the rough-type *mycobacterium*.

In some aspects, detecting the smooth-type *mycobacterium* comprises detecting a protein, lipid or polysaccharide preferentially expressed by the smooth-type *mycobacterium*. In a particular aspect, detecting the smooth-type *mycobacterium* comprises detecting a lipid preferentially expressed by the smooth-type *mycobacterium*. In another particular aspect, detecting the smooth-type *mycobacterium* comprises detecting a polysaccharide preferentially expressed by the smooth-type *mycobacterium*. In yet another particular aspect, detecting the smooth-type *mycobacterium* comprises detecting a protein preferentially expressed by the smooth-type *mycobacterium*.

Proteins, lipids, polysaccharides and genes that can be used to detect R-type or S-type *mycobacterium* (e.g., *M. tuberculosis*) include those described above with respect to the assays. In some aspects, the protein, lipid or polysaccharide preferentially expressed by the rough-type *mycobacterium* is a cell surface protein, lipid or polysaccharide. In other aspects, the protein, lipid or polysaccharide preferentially expressed by the smooth-type *mycobacterium* is a cell surface protein, lipid or polysaccharide. In some aspects, the protein, lipid or polysaccharide preferentially expressed by the rough-type *mycobacterium* is a cell surface protein, lipid or polysaccharide, and the protein, lipid or polysaccharide preferentially expressed by the smooth-type *mycobacterium* is a cell surface protein, lipid or polysaccharide.

In some aspects, detecting the rough-type *mycobacterium* comprises detecting a molecule preferentially secreted by the rough-type *mycobacterium*. In other aspects, detecting the smooth-type *mycobacterium* comprises detecting a molecule preferentially secreted by the smooth-type *mycobac-*

*terium*. In some aspects, detecting the rough-type *mycobacterium* comprises detecting a molecule preferentially secreted by the rough-type *mycobacterium* and detecting the smooth-type *mycobacterium* comprises detecting a molecule preferentially secreted by the smooth-type *mycobacterium.*

In some aspects, detecting the rough-type *mycobacterium* comprises detecting a cytokine (e.g., a cytokine released from a T-cell lymphocyte, such as interferon gamma) induced by a first molecule (e.g., antigen, such as a protein, lipid or polysaccharide, or a combination of any of the foregoing molecules) from the rough-type *mycobacterium*. In other aspects, detecting the smooth-type *mycobacterium* comprises detecting a cytokine (e.g., a cytokine released from a T-cell lymphocyte, such as interferon gamma) induced by a second molecule (e.g., antigen, such as a protein, lipid or polysaccharide, or a combination of any of the foregoing molecules) from the smooth-type *mycobacterium*. In some aspects, detecting the rough-type *mycobacterium* comprises detecting a cytokine (e.g., a cytokine released from a T-cell lymphocyte, such as interferon gamma) induced by a first molecule (e.g., antigen, such as a protein, lipid or polysaccharide, or a combination of any of the foregoing molecules) from the rough-type *mycobacterium*, and detecting the smooth-type *mycobacterium* comprises detecting a cytokine (e.g., a cytokine released from a T-cell lymphocyte, such as interferon gamma) induced by a second molecule (e.g., antigen, such as a protein, lipid or polysaccharide, or a combination of any of the foregoing molecules) from the smooth-type *mycobacterium.*

When the method involves detecting a cytokine, the method can further comprise providing a molecule immobilized on a first surface and a second surface that binds to the cytokine, wherein the first surface and the second surface are independently detectable; providing a detectable molecule that binds to the cytokine; exposing the first surface to sample, the first molecule and the detectable molecule under conditions suitable to form an immobilized molecule-cytokine-detectable molecule conjugate immobilized on the first surface; and exposing the second surface to sample, the second molecule and the detectable molecule under conditions suitable to form an immobilized molecule-cytokine-detectable molecule conjugate immobilized on the second surface. Presence of the rough-type *mycobacterium* is indicated by presence of the detectable molecule on the first surface, and presence of the smooth-type *mycobacterium* is indicated by presence of the detectable molecule on the second surface.

In some aspects, the method further comprises incubating the sample with a first molecule that selectively binds to the rough-type *mycobacterium*, and detecting the rough-type *mycobacterium* by detecting the first molecule. In other aspects, the method further comprises incubating the sample with a second molecule that selectively binds to the smooth-type *mycobacterium*, and detecting the smooth-type *mycobacterium* by detecting the second molecule. In some aspects, the method further comprises incubating the sample with a first molecule that selectively binds to the rough-type *mycobacterium*, and detecting the rough-type *mycobacterium* by detecting the first molecule; and incubating the sample with a second molecule that selectively binds to the smooth-type *mycobacterium*, and detecting the smooth-type *mycobacterium* by detecting the second molecule.

In some aspects, the method further comprises incubating the sample with a first molecule that binds to a molecule preferentially secreted by the rough-type *mycobacterium*, and detecting the rough-type *mycobacterium* by detecting the first molecule. In other aspects, the method further comprises incubating the sample with a second molecule that binds to a molecule preferentially secreted by the smooth-type *mycobacterium*, and detecting the smooth-type *mycobacterium* by detecting the second molecule. In some aspects, the method further comprises incubating the sample with a first molecule that binds to a molecule preferentially secreted by the rough-type *mycobacterium*, and detecting the rough-type *mycobacterium* by detecting the first molecule; and incubating the sample with a second molecule that binds to a molecule preferentially secreted by the smooth-type *mycobacterium*, and detecting the smooth-type *mycobacterium* by detecting the second molecule.

In some aspects of the methods, the first molecule is a monoclonal antibody. In other aspects, the second molecule is a monoclonal antibody. In some aspects, the first molecule is a monoclonal antibody and the second molecule is a monoclonal antibody. Other molecules useful in the methods described herein are as described with respect to the assays.

In some aspects, the methods comprise providing a sample; detecting a *mycobacterium* described herein (e.g., *M. tuberculosis*) in the sample (e.g., according to known methods, such as a TST or sputum smear microscopy); and independently detecting rough-type *mycobacterium* and smooth-type *mycobacterium* in the sample, wherein presence of the rough-type *mycobacterium* and the smooth-type *mycobacterium* indicates active infection and presence of the rough-type *mycobacterium* and absence of the smooth-type *mycobacterium* indicates latent infection.

TB infection can also be detected using any of the assays described herein.

EXEMPLIFICATION

Example 1

Chemicals and Reagents.

Middlebrook 7H9 and 7H10 media were purchased from Difco (BD Franklin Lakes, N.J.), OADC was from Difco or made in house (19), Tween 80 was from Sigma-Aldrich (St. Louis, Mo.), Phosphate Buffered Saline (PBS) was from Gibco (Thermo Fisher Scientific, Agawam, Mass.). Restriction enzymes were purchased from New England Biolabs (Ipswich, Mass.).

Bacterial Strains and Culture:

Bacterial strains used in this study are listed in Table 1. Standard media and culture conditions were as described ( )Dubos 1947; Larsen 2007) with modifications (+/−Tween at 0.05%) described in the text. Each 7H10 agar plate prepared using standard plastic petri dish (100×15 mm) with 25 ml of molten 7H10 agar with supplements. *M. smegmatis* $mc^2155$ was cultured in Middlebrook 7H9 or 7H10. *M. tuberculosis* and *M. bovis* were cultured in Middlebrook 7H9 or 7H10 supplemented with 10% OADC. Carbon sources were slightly modified from standard Middlebrook (BD): Glycerol was at a final concentration of 0.5% (Middlebrook calls for 0.2%); glucose was at a final concentration 0.2% (which is the normal amount). Delta-RD1 strains of *M. tuberculosis* H37Rv and Erdman, and *M. bovis* Ravenal (Hsu 2003) were cultured with the Middlebrook media as described above. *M. tuberculosis* ΔRD1 ΔpanCD strains (Sambandamurthy 2006) were cultured in media supplemented with 50 μg/ml D-pantothenic acid. *E. coli* DH5a was cultured in LB media (Green 2012). Hygromycin was added to the medium at 50 μg/ml concentration for growing mycobacteria and at 150 μg/ml concentration for growing *E. coli*. Kanamycin was used at 20 μg/ml for mycobacteria and at 40 μg/ml for *E. coli.*

TABLE 1

| Bacterial Strains Used in this Study. | | | |
|---|---|---|---|
| Strain Name | Parent Strain | Genotype | Reference |
| H37Rv | *M. tuberculosis* | Wild type | Steenken 1934; Hsu 2003; Steenken 1946 |
| Erdman | *M. tuberculosis* | Wild type | Hsu 2003 |
| CDC1551 | *M. tuberculosis* | Wild type | Hsu 2003 |
| Ravanel | *M. bovis* | Wild type | Hsu 2003 |
| $mc^2$4002 | H37Rv | ΔRD1 | Hsu 2003 |
| $mc^2$4023 | Erdman | ΔRD1 | Hsu 2003 |
| $mc^2$4024 | CDC1551 | ΔRD1 | Hsu 2003 |
| $mc^2$4101 | Ravanel | ΔRD1 | Hsu 2003 |
| $mc^2$6030* | H37Rv | ΔRD1 ΔPanCD (unmarked) | Larsen 2009 |
| $mc^2$6230* | H37Rv | ΔRD1 ΔPanCD (unmarked) | Vilcheze 2013 |
| $mc^2$7000* | $mc^2$4002 | ΔRD1 ΔPanCD (unmarked) | Sambandamurthy 2006 |
| Pasteur | *M. bovis* BCG | Laboratory adapted strains | W. R. Jacobs. Jr. |
| $mc^2$155 | *M. smegmatis* | eptC1 A > T | Snapper 1990 |

Molecular Biology:

Southern hybridization, molecular cloning and gene transfer procedures were performed according to standard methods (Green 2012). DNA manipulation and plasmid construction procedures were performed in the *E. coli* strain DH5a. Genetic manipulations of mycobacteria that include transformation and transduction were as described (Larsen 2007; Jain 2014). Procedures of cloning, complementation and Southern blotting of the RD1 region were performed as described (Hsu 2003).

Single-Cell Preparation and the Growth of S- and R-Type Colony on Agar Plates:

Single-cell preparations were made in any of three ways: (1) from freezer stocks of liquid cultures. In some cases, these were brought to 1 ml by addition of fresh PBS. In other cases, where a full ml of frozen culture was available, there was no addition of PBS. In all cases, thawing with or without PBS addition was followed by vortexing for circa 20 seconds at full speed on a desktop analog vortex mixer (VWR Model 58816-123) followed by gravity-mediated passage through sterile 5-μm nylon syringe filters (GE Water & Process Technologies Catalog No. DDR5002550). Usually gravity was enough and the filtrate penetrated in a few seconds but sometimes the filter apparently became a little clogged and the plunger of the syringe was inserted to moderately increase pressure and get the filtrate through. The filter was not broken; (2) from 0.1 ml of fresh liquid culture mixed with 0.9 ml of PBS or from 1 ml of growing liquid culture without addition of PBS. Filtration the same as described for frozen and thawed samples; or (3) single cell/small aggregate preparations from single colonies grown on 7H10 agar plates were prepared by picking each single colony into a separate 2 ml screw-cap tube containing 1 ml of PBS and 0.3 gram of zirconia silica beads (0.1 mm, Biospec Cat. No. 11079101z). The tube was vortexed for 20 seconds at full speed, beads were allowed to settle, and the supernatant was passed through a 5-μm filter by gravity. The filtrate was serially diluted in PBS and aliquots spread on 7H10 OADC agar plates. Plates were wrapped in aluminum foil and incubated aerobically at 37° C.

Determination of Wet Weight of S- and R-Type Colonies:

Single-cell suspensions were prepared from liquid cultures of $mc^2$6230, followed by plating dilutions on 7H10NT OADC agar. Plates were incubated aerobically at 37° C. for 4 weeks. Ten plates per experiment were used for weighing with each plate containing between 22 and 57 colonies. All colonies on each plate were divided into colony types and used in the weighing. (When there were more colonies grown on a plate, then the size of individual colonies tended to be smaller as colonies grew close to each other. These plates were not analyzed further.) Colonies were lifted off the agar with a sharpened spatula. All the colonies on each individual plate were pooled by morphotype into pre-weighed 15 ml conical tubes. Separate tubes were used for each plate and each colony type. Care was taken to avoid picking up agar underneath each colony. Both Spread and Raised colonies of mycobacteria were strongly self-adherent and each colony could be cleanly lifted off the agar as an intact unit. Plates for each experiment were in a single foil-wrapped stack. The average weight of S- and R-type colonies from each plate was calculated.

Microarray Analysis:

Proper dilutions of single cell preparation from a liquid culture of $mc^2$7000 (Mtb ΔRD1 ΔpanCD) were spread on 7H10 OADC agar plates supplemented with D-pantothenic acid at 24 μg/ml, and incubated at 37° C. for 4 weeks. Colonies of S- and R morphotypes were identified and picked into separate conical tubes. Approximately 0.5 gram of bacterial colonies (wet weight) were re-suspended in 1 ml of buffer RLT and processed with a Qiagen RNeasy kit. Microarray analysis was performed as described (Jain 2016).

Accession Number(s):

Microarray data have been deposited in NCBI GEO under accession number GSE89089.

Figure 1B:
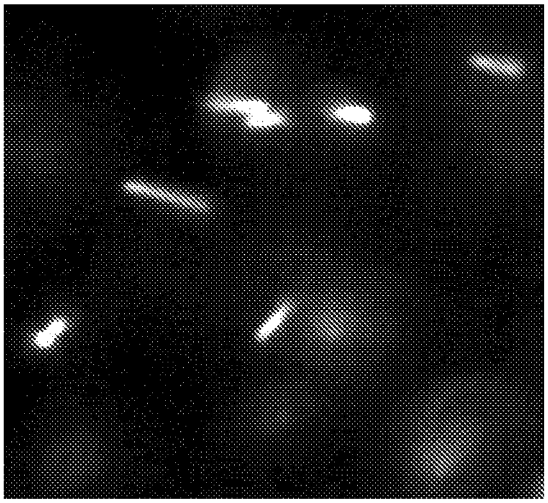
FIG. 1B is an image taken on a fluorescence microscope of the $mc^2155$ (*M. smegmatis*) liquid culture pictured in FIG. 1A after passing through a 5-μm filter.

Results:

Single cell suspensions were prepared by (1) passing vortexed liquid cultures either fresh or frozen and thawed through 5-μm filters; or (2) re-suspending a single colony in PBS, breaking it up by vortexing and then passing the suspension through a 5-μm filter. The starting liquid cultures contained tightly adhering mycobacterial aggregates (FIG. 1A), but the 5 μm filtrate contained largely single cells or much smaller aggregates (FIG. 1B), as confirmed by microscopy. Dilutions of these single cell and small aggregate suspensions were spread on plates; the plates were wrapped in aluminum foil, and incubated aerobically at 37° C.

Colonies arising from single cell small aggregate suspensions were more uniform compared to those from unfiltered liquid cultures. H37Rv (Ioerger 2010) appeared to yield colonies of a single morphotype and size (FIG. 2A). In the course of constructing $mc^2$4002, RD1 deletion mutants of H37Rv, two distinct colony morphotypes became evident: spread (S-type) and raised (R-type) (FIG. 2B; arrow indicates R-type, magnified as in FIG. 2F at four weeks and FIG. 2G at eight weeks). R-types were originally small, raised with a hollow center and eventually developed into colonies with large rims, while S-types retained the same round and flat shape, often with a fried egg center, irrespective of the age of the colony. An early concern was that the ΔRD1 deletion might not be present in all cells or that the $mc^2$4002 culture had become contaminated. Two results show that this was not the case: (1) $mc^2$4002 complemented with RD1 sequence gave rise to 100% S-type colonies (FIG. 2C), and (2) both S- and R-type of $mc^2$4002 carried the RD1 deletion, as demonstrated by DNA hybridization (FIG. 2D). The shape of spread morphotype colonies (FIG. 2E) was constant as they grew, whereas raised morphotype colonies varied more (e.g., FIGS. 2F and 2G).

Figure 3A:
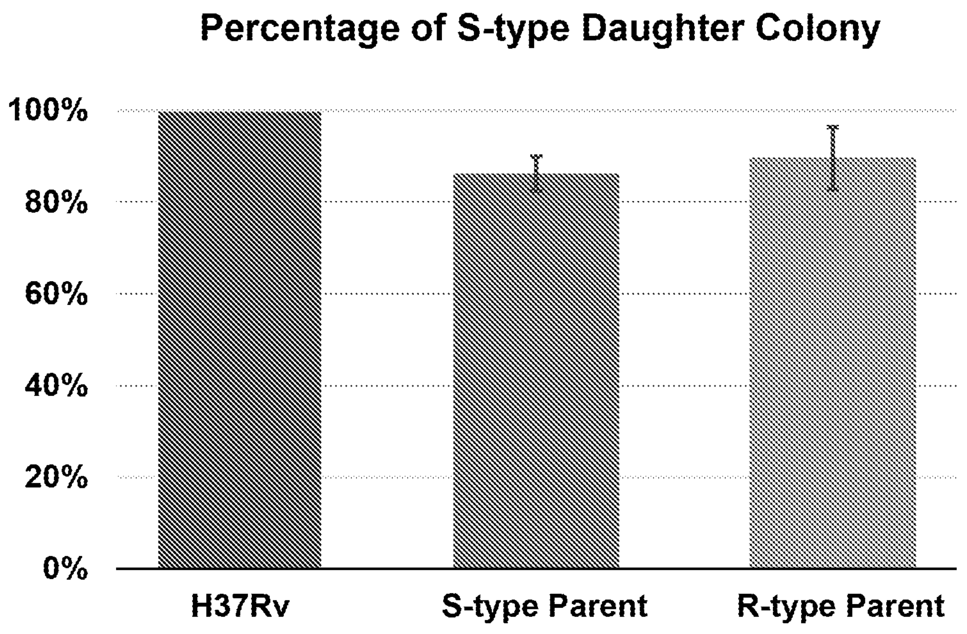
FIG. 3A shows the distribution of colonies of S and R morphotypes in liquid culture of $mc^24002$. Three independent colonies of either S or R morphotype of $mc^24002$ (H37Rv ΔRD1) were identified and inoculated into 7H9 OADC. The cultures were grown at 37° C. until O.D. reached 1.0. One-tenth milliliter (0.1 ml) of each culture was added to 0.9 ml of PBS and allowed to pass through a 5-μm filter by gravity. Each filtrate was serially diluted with PBS and spread on 7H10 OADC agar plates. Plates with colony numbers between 50 and 200 were chosen for enumeration to determine the cfu of each morphotype. Percentage of S-type colonies derived from three liquid cultures of each colony morphotype was calculated based on the combined number of colonies on two agar plates spread with the same amount of dilution. One culture of wild type H37Rv served as control. See FIG. 3B for the distribution and number of colonies of each morphotype detected on each plate.
Figure 3B:
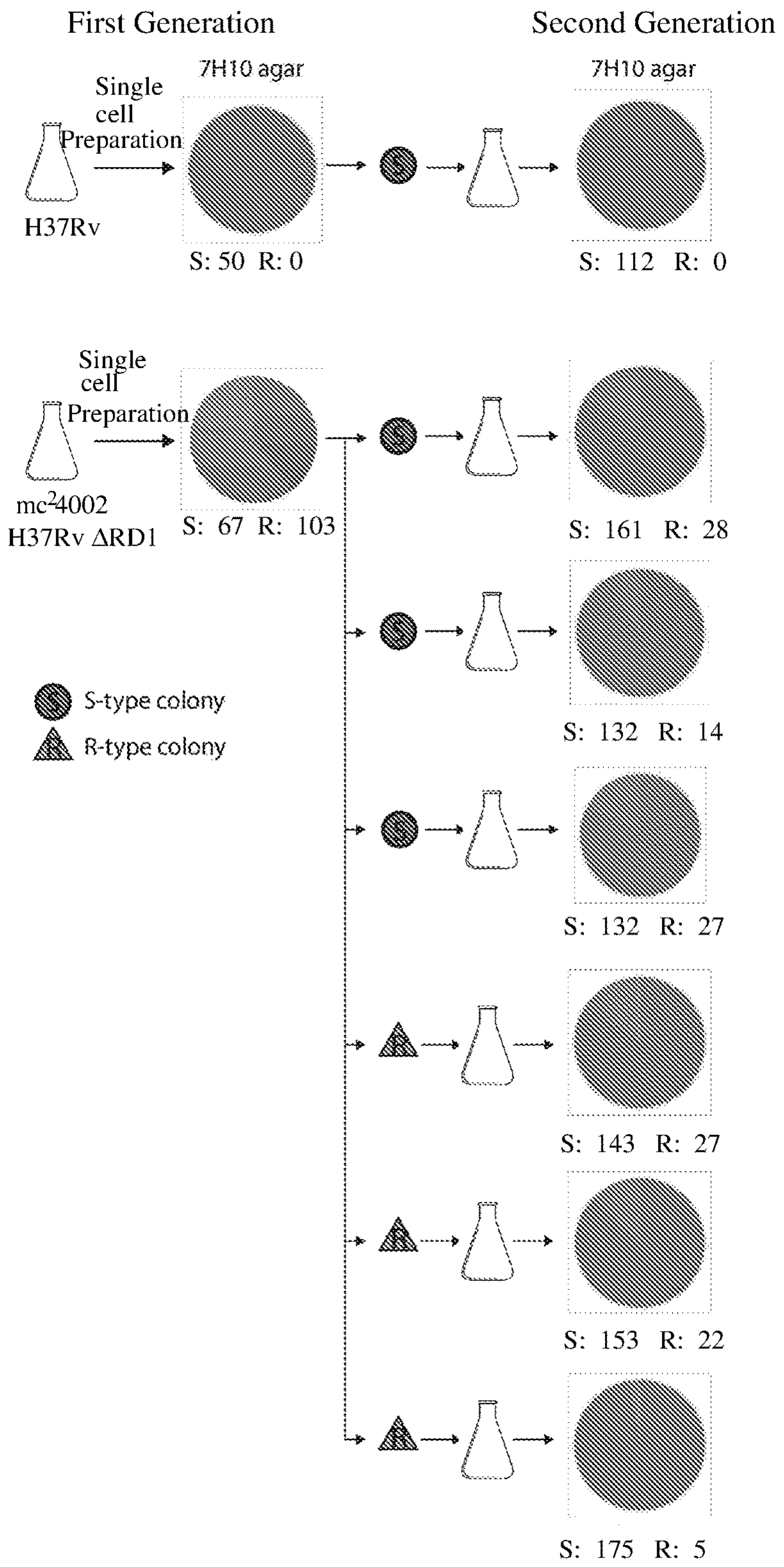
FIG. 3B shows the distribution of colonies of S and R morphotypes in liquid culture of $mc^24002$. Freezer stock was inoculated into 7H9 OADC liquid medium supplemented with 0.05% Tween. After confluent growth, serial dilutions of single cell preparation were spread on 7H10 OADC agar plates followed by incubation at 37° C. for 4 weeks. Distinct S- or R-type colonies were enumerated for each agar plate, represented as numbers of each colony type beneath each plate. For H37Rv, it was 100% S-type. Numbers beneath each plate were the sum of two identical plates spread with 111 μl of the same diluent of the single cell preparation of each liquid culture. For H37Rv ΔRD1, in the first generation there were 67 S-type and 103 R-type colonies on plates spread with diluents that were diluted 10,000 fold. For the second generation, three colonies of each type from the first generation were inoculated separately into 7H9 OADC liquid media supplemented with 0.05% Tween followed by single cell preparation and spreading of filtrates on 7H10 OADC agar plates. Results of the distribution of colony of each type for the second generation are shown and were derived from plates spread with diluents diluted 100,000 fold.
Figure 5A:
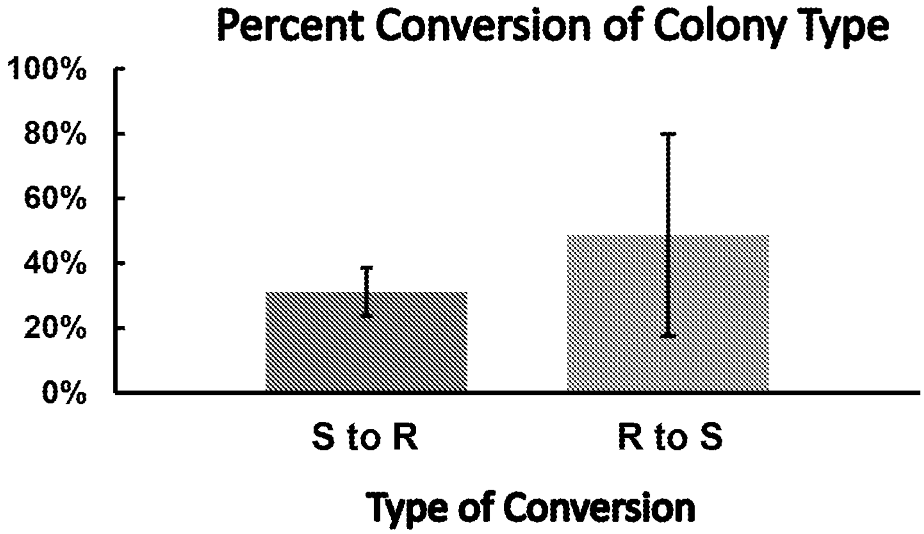
FIG. 5A shows the phase conversion of colonies. Single cell/small aggregate preparations of $mc^2$7000::Tn were serially diluted and spread on 7H10 OADC agar plates supplemented with 24 μg/ml D-pantothenic acid. Ten (10) colonies of each morphotype were identified and made into single cell/small aggregate preparations. These preparations were serially diluted and spread on 7H10 OADC plates supplemented with D-pantothenic acid at 24 μg/ml and incubated at 37° C. for 4-6 weeks. S and R morphotype colonies were counted and conversion rate with standard error was calculated. Results are presented as percent conversion either from S-type to R-type or visa versa.
Figure 5B:
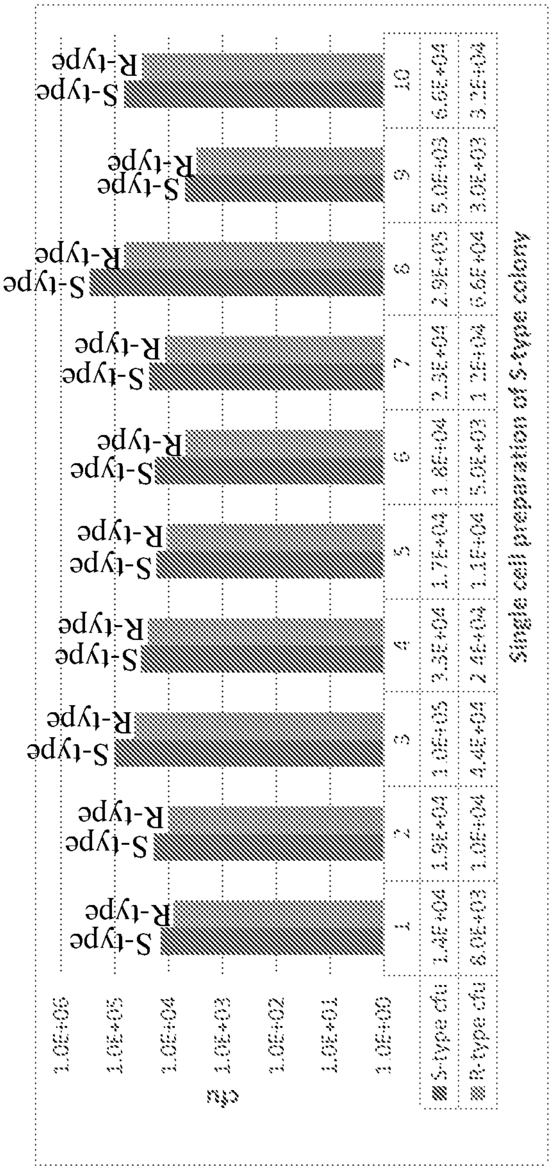
FIG. 5B shows the distribution of colonies of S and R morphotypes in the single-cell preparations made from a single colony of S or R morphotype. Single-cell preparations made with a liquid culture of a mariner transposon library of $mc^2$7000 were spread on 7H10 agar plates supplemented with 24 μg/ml of D-pantothenic acid. Ten (10) colonies of each morphotype were identified and separately made into single-cell preparations, serially diluted, and spread on the same 7H10 agar plates. The number of colonies of each morphotype grown on each agar plate was determined and is presented in log scale. The number on the bottom indicates the number of colonies of each morphotype counted in agar plates spread with the proper dilution of single-cell preparations.
Figure 5B:
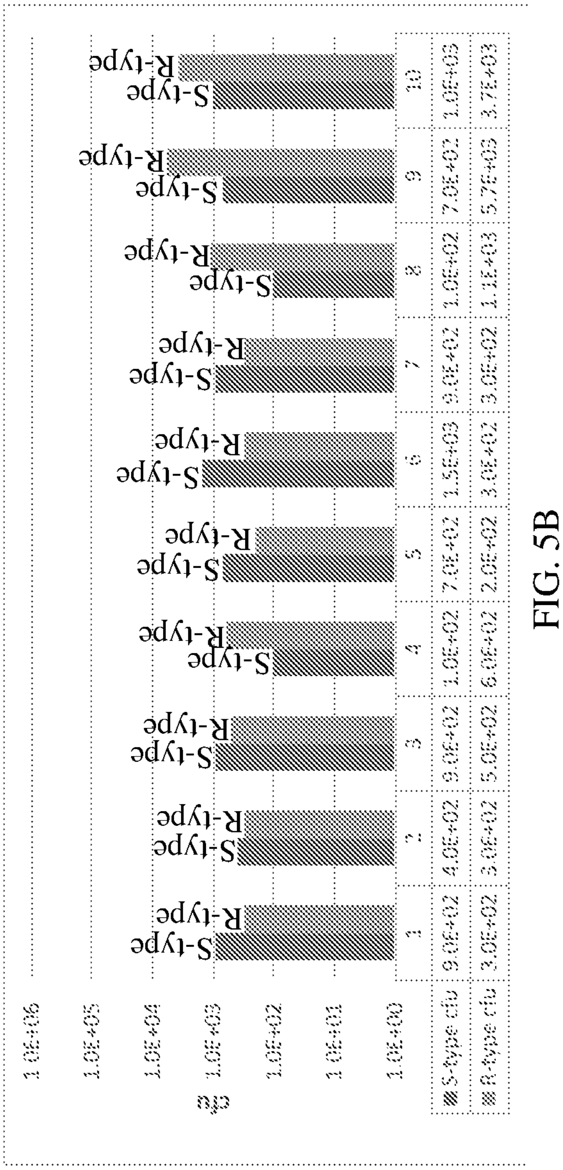

Phase variation means that some cells from a colony of the S morphotype, will give rise to colonies of the R morphotype and visa versa. The hypothesis of phase variation was tested in both directions. The vortex and filtration procedures were repeated to make new colonies from single cells derived from "mother" colonies of each morphotype. As shown in FIGS. 3A and 3B, 5 μm filtrates of liquid cultures grown from S-type or R-type colonies of *M. tuberculosis* ΔRD1 produced both S-type (about 80%) and R-type (about 20%) colonies on 7H10 OADC agar plates whether R- or S-type colonies were used as the inoculum. Wild type *M. tuberculosis* produced only S-type colonies on the same medium.

Figure 4A:
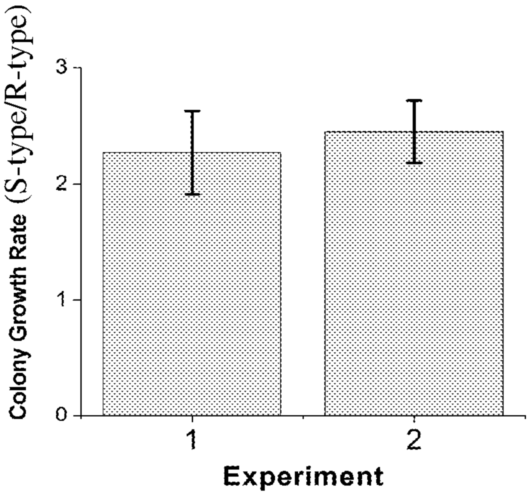
FIG. 4A shows the comparative weights of colonies of S and R morphotypes. 5 μm filtrates of $mc^2$6230 (H37Rv ΔRD1 ΔpanCD) were serially diluted and spread on 7H10 OADC agar plates supplemented with D-pantothenic acid at 48 μg/ml and incubated aerated at 37° C. for 4 weeks. Ten (10) agar plates with well-separated colonies were identified. On each agar plate, all the colonies of the same morphotype were pooled into a conical tube and their collected weight was determined. Then the ratio of the average weight of S-type colonies compared to R-type colonies on each agar plate was calculated. Standard errors were also determined from data derived from 10 agar plates.
Figure 4B:
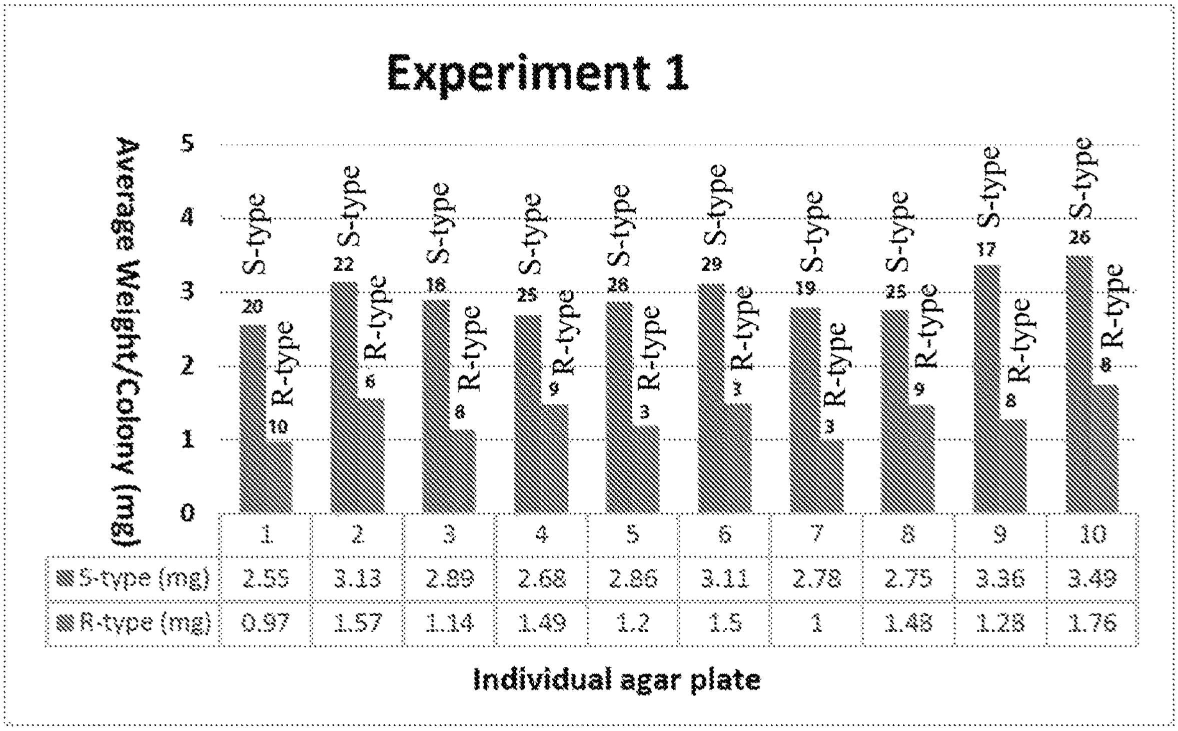
FIG. 4B shows the results of a comparative study of growth rate of colonies of S and R morphotypes. Colonies of $mc^2$6230 (*M. tuberculosis* ΔRD1 ΔPanCD) grown aerobically on each of ten (10) 7H10 OADC agar plates supplemented with pantothenic acid at 48 μg/ml were identified as either S- or R-type, collectively pooled into separate 15-ml conical tubes and weighed. The average weight of colonies of either S or R morphotype was determined based on the number of colonies collected in each conical tube. The experiment was performed twice. The number on top of each bar represents the number of colonies of S- or R-type found on the 7H10 OADC agar plate. The number on the bottom indicates the average weight in milligrams of each type of colony.
Figure 4B:
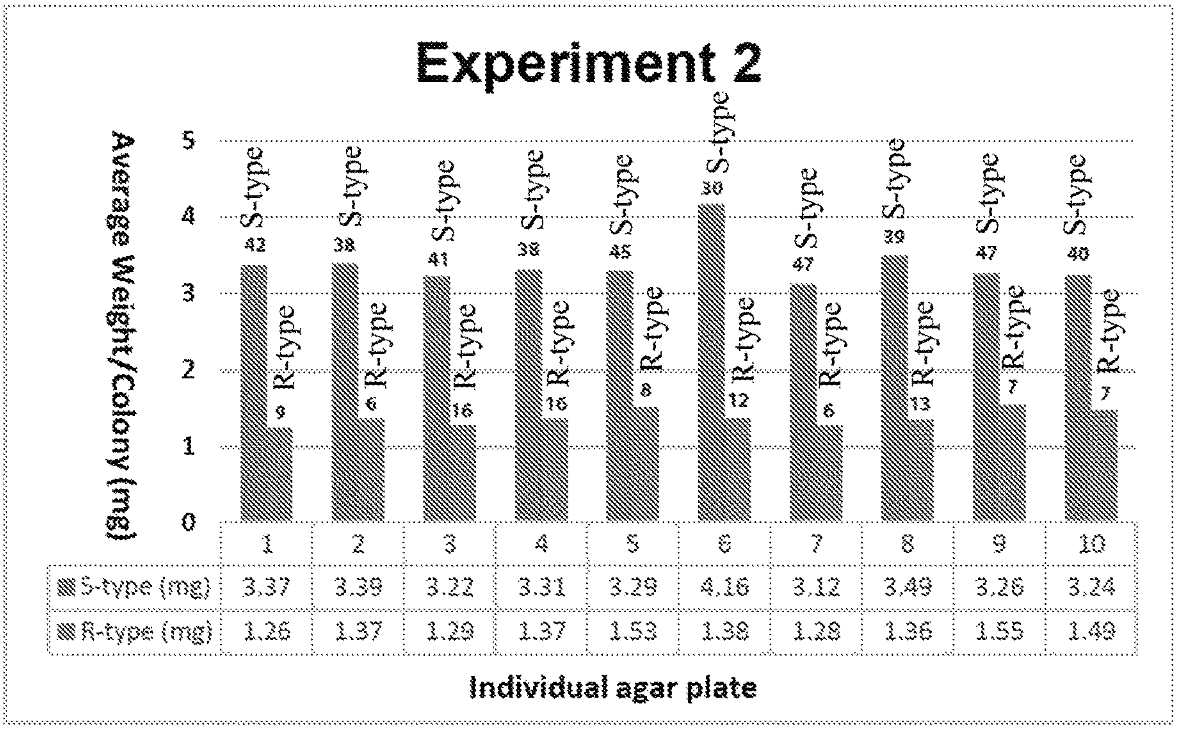

S-type $mc^2$4002 (H37Rv ΔRD1) dominated the population in liquid cultures, by hypothesis, because it grew faster. This hypothesis suggested that S-type colonies might also grow faster. Serial dilutions of single cell/small aggregate preparations of liquid culture of $mc^2$6230 (H37Rv ΔRD1 ΔpanCD) were spread on 7H10 OADC agar plates supplemented with D-pantothenic acid. After 4-weeks incubation at 37° C., 10 individual plates containing colony numbers ranging from 22 to 34 for the first experiment and from 42 to 64 for the second experiment were included in the experiments. Plates with more colonies than those chosen were excluded because colony crowding led to smaller colonies. All colonies on the included plates were used in the analysis. The distribution of S- and R-type colonies on these plates was consistent with that seen previously. Pooled colonies were used to obtain and compare the average colony weight of S- and R-morphotypes. At four weeks 37° C. aerobic incubation S-type colonies weighed approximately twice as much as the R-type colonies (FIG. 4A). S colonies averaged per plate ranged from approximately 2.5 to 3.5 mg per colony while R colonies on the same plates had averages ranging from approximately 1.0 to 1.5 mg per colony (FIG. 4B).

Phase conversion was assayed with members of a $mc^2$7000 (H37Rv ΔRD1 ΔpanCD) mariner transposon library ($mc^2$7000::Tn). Whole colonies of S-type and R-type $mc^2$7000::Tn were lifted directly from 7H10 OADC agar plates into separate 2 ml screw-cap tubes, added to PBS, vortexed at full speed for 20 seconds at the presence of zirconia beads, passed through a 5-μm filter to obtain single cell small aggregate suspensions, dilutions spread on 7H10 OADC agar plates, incubated, and S- and R-morphotype progeny were scored. Similar frequencies of S-type and R-type colonies were obtained from parent colonies of either type (FIGS. 5A and 5B). S-type colonies put through the single cell small aggregate suspension procedure yielded $10^4$-$10^5$ CFU/colony. R-type colonies yielded $10^3$-$10^4$ CFU/colony, an order of magnitude less CFU per original colony (FIG. 5B).

Wild type *M. tuberculosis* H37Rv was initially judged to make only S-type colonies on 7H10 OADC agar plates. Subsequently, a subtle but distinct morphotype variation that was visible on 7H10 OADC agar plates supplemented with Tween 80 at 0.05% was noticed, suggesting the Tween 80 modifies colony morphology of Mtb. The S-type colonies on Tween agar plate fell into one of two distinct types, one with a raised center and one without.

Figure 6:
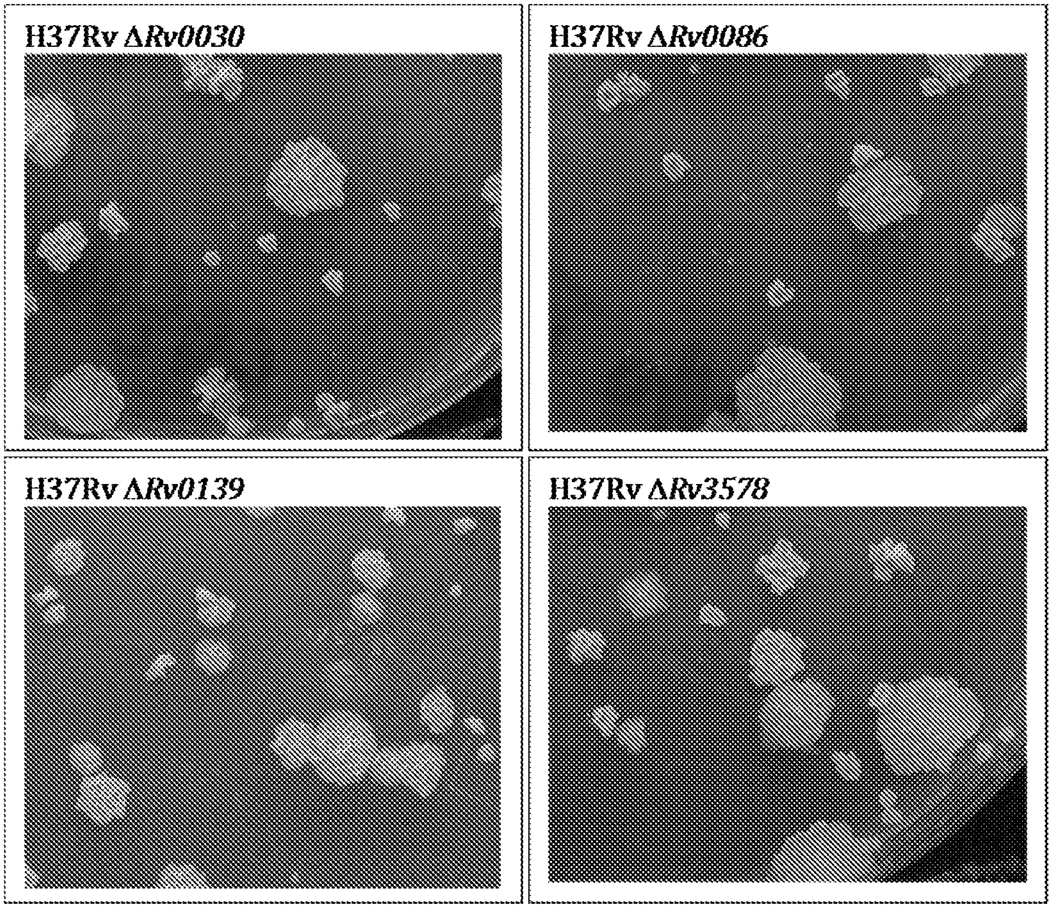
FIG. 6 shows colonies of R and S morphotypes in non-RD1 null-deletion mutants (ΔRv0030, ΔRv0086, ΔRv0139, ΔRv3578) of H37Rv. H37Rv cultures transduced with specialized transducing phages and spread on 7H10 OADC agar plates supplemented with 50 μg/ml hygromycin.

Successful specialized transduction requires a relatively rare double-crossover homologous recombination event. Under appropriate plating conditions each colony is likely the result of an independent transduction event and each fully drug resistant colony is therefore likely to be clonal, i.e. to be the progeny of a single transduced cell. The two distinct morphotypes were also observed when many other defined null deletions were introduced into H37Rv by specialized transduction (FIG. 6). Thus, the two colony morphotypes occurred independently of the RD1 deletion and were also seen in many strains that were wild type for the RD1 locus. Several other mycobacterial strains and species also were found with the two distinct S and R morphotypes including $mc^2$4023 (Erdman ΔRD1) and $mc^2$4101 (Ravenel ΔRD1), similar to the S- and R-type colonies of $mc^2$4002 (H37Rv ΔRD1). BCG also carries an RD1 deletion and displayed both S- and R-type colonies. BCG was unique in that S and R morphotypes were equally apparent whether or not the plating medium contained Tween 80. *M. smegmatis* $mc^2$155 is so far the only mycobacterial species outside *M. tuberculosis* for which phase variation has been rigorously demonstrated by spreading dilutions of single cell small aggregate suspensions made from liquid regrowth of defined colonies of S and R types.

Mixed or sectored colonies displaying both S- and R-type characteristics were never observed. As soon as an incipient colony was barely visible it was stably one morphotype. This implied that the morphotype was "locked in" once colonies had begun to form on agar. Although the molecular mechanism of this apparent "locking in" is unknown at present, it allowed the study of gene expression profiles by isolating RNA directly from colonies of S- and R-type. As shown in Table 2, colonies of the R morphotype of $mc^2$7000 were most up-regulated for the DosR regulon and other hypoxia-associated genes. In contrast, S morphotype mRNA was consistent with aerobic growth (Table 3).

TABLE 2

Genes up-regulated by at least 2 fold in the R-type colonies of H37Rv (*M. tuberculosis* ΔRD1 ΔpanCD), compared to S-type.

| Rv No. | Product | Gene Name | Regulon | Fold Increased |
|---|---|---|---|---|
| Rv2623 | Universal stress protein family protein TB31.7 | TB31.7 | DosR | 3.93 |
| Rv2007c | Ferredoxin FdxA | fdxA | DosR | 3.83 |
| Rv1738 | Conserved protein | Rv1738 | DosR | 3.62 |
| Rv2626c | Hypoxic response protein 1 Hrp1 | Rv2626c | DosR | 3.55 |
| Rv0079 | Unknown protein | Rv0079 | DosR | 3.32 |
| Rv2032 | Conserved protein Acg | acg | DosR | 3.20 |
| Rv3418c | 10 kDa chaperonin GroES | groES | | 3.17 |
| Rv0440 | 60 kDa chaperonin 2 GroEL2 | groE2 | | 3.05 |
| Rv2030c | Conserved protein | Rv2030c | DosR | 2.97 |
| Rv1736c | Probable nitrate reductase NarX | narX | DosR | 2.85 |
| Rv1996 | Universal stress protein family protein | Rv1996 | DosR | 2.72 |
| Rv2624c | Universal stress protein family protein | Rv2624c | DosR | 2.65 |
| Rv0080 | Conserved hypothetical protein | Rv0080 | DosR | 2.65 |
| Rv2627c | Conserved protein | Rv2627c | DosR | 2.63 |

TABLE 2-continued

Genes up-regulated by at least 2 fold in the R-type colonies of H37Rv (*M. tuberculosis* ΔRD1 ΔpanCD), compared to S-type.

| Rv No. | Product | Gene Name | Regulon | Fold Increased |
|---|---|---|---|---|
| Rv0467 | Isocitrate lyase IclI | icl1 | | 2.63 |
| Rv3131 | Conserved protein | Rv3131 | DosR | 2.60 |
| Rv1221 | Alternative RNA polymerase sigma factor SigE | sigE | MprA | 2.54 |
| Rv2710 | RNA polymerase sigma factor SigB | sigB | MprA | 2.49 |
| Rv2031c | Heat shock protein HspX | hspX | DosR | 2.43 |
| Rv2382c | Polyketide synthetase MbtC | mbtC | | 2.36 |
| Rv2005c | Universal stress protein family protein | Rv2005c | DosR | 2.35 |
| Rv3127 | Conserved protein | Rv3127 | DosR | 2.33 |
| Rv2625c | Probable conserved transmembrane alanine and leucine rich protein | Rv2625c | DosR | 2.32 |
| Rv3130c | Triacylglycerol synthase TgsI | tgsI | DosR | 2.30 |
| Rv3290c | Probable L-lysine-epsilon aminotransferase Lat | lat | | 2.28 |
| Rv2621c | Possible transcriptional regulatory protein | Rv2621c | | 2.25 |
| Rv2629 | Conserved protein | Rv2629 | DosR | 2.21 |
| Rv1733c | Probable conserved transmembrane protein | Rv1733c | DosR | 2.17 |
| Rv2029c | 6-phosphofructokinase PfkB | pfkB | DosR | 2.12 |
| Rv2271 | hypothetical protein | Rv2271 | RelA | 2.06 |
| Rv0572c | Hypothetical protein | Rv0572c | DosR | 2.04 |
| Rv3354 | Conserved hypothetical protein | Rv3354 | | 2.04 |
| Rv2912c | Probable transcriptional regulatory protein | Rv2912c | | 2.03 |
| Rv2628 | Hypothetical protein | Rv2628 | DosR | 2.02 |
| Rv2028c | Universal stress protein family protein | Rv2028c | DosR | 2.01 |
| Rv3126c | Hypothetical protein | Rv3126c | DosR | 2.01 |

TABLE 3

Genes up-regulated by at least 2 fold in the S-type colonies of H37Rv (*M. tuberculosis* ΔRD1 ΔpanCD), compared to R-type.

| Rv No. | Product | Gene name | Regulon | Fold Increased |
|---|---|---|---|---|
| Rv0994 | Probable molybdopterin biosynthesis protein MoeA1 | moeA1 | | 3.15 |
| Rv1132 | Conserved membrane protein | Rv1132 | KstR | 2.84 |
| Rv1195 | PE family protein PE13 | pe13 | RelA | 2.83 |
| Rv2817c | Conserved hypothetical protein | Rv2817c | Rv1404 | 2.55 |
| Rv0514 | Possible transmembrane protein | Rv0514 | | 2.43 |
| Rv2782c | Probable zinc protease PepR | pepR | | 2.43 |
| Rv3662c | Conserved hypothetical protein | Rv3662c | | 2.39 |
| Rv2988c | Probable 3-isopropylmalate dehydratase (large subunit) LeuC | leuC | | 2.33 |
| Rv3409c | Cholesterol oxidase ChoD | choD | | 2.32 |
| Rv1905c | Probable D-amino acid oxidase Aao | Aao | | 2.25 |
| Rv0242c | Probable 3-oxoacyl-[acyl-carrier protein] reductase FabG4 | fabG | | 2.23 |
| Rv2074 | Possible pyridoxamine 5'-phosphate oxidase (PNP/PMP oxidase) | Rv2074 | | 2.19 |
| Rv1644 | Possible 23S rRNA methyltransferase tsnR | tsnR | | 2.14 |
| Rv2987c | Probable 3-isopropylmalate dehydratase (small subunit) LeuD | leuD | | 2.13 |
| Rv2431c | PE family protein PE25 | pe25 | | 2.07 |
| Rv2060 | Possible conserved integral membrane protein | Rv2060 | Zur | 2.06 |
| Rv1047 | Probable transposase | Rv1047 | | 2.03 |
| Rv3582c | 4-diphosphocytidyl-2C-methyl-D-erythritol synthase IspD (MEP cytidylyltransferase) | ispD | | 2.03 |
| Rv2809 | Hypothetical protein | Rv2809 | | 2.02 |

Phase variation was rigorously demonstrated in several strains of *M. tuberculosis*, in *Bacillus* Calmette-Guerin Pasteur (BCG Pasteur) and in *M. smegmatis* $mc^2155$. A dimorphic appearance of colonies was seen after plating single cell/small aggregate suspensions, and after specialized transduction. Phase variation is likely common in mycobacteria. Previous observations of phase variation in mycobacteria have likely been obscured because variable aggregates of cells give rise to a confusing heterogeneity of colony sizes and shapes. When CFUs were single cells and/or small aggregates, then distinct colony morphotypes were observed with several different strains, genotypes, and species. Specialized transduction is another route through which macroscopic mycobacterial colonies start from single cells and the same two distinct morphotypes were often observed.

S (spread) morphotype colonies accumulated twice the mass of R (raised) morphotype colonies. Three alternative possibilities could account for the greater weight of S morphotype colonies: (1) cells in S morphotype colonies may have a faster doubling time so that the colony weight represent the number of cells in the colony; (2) S morphotype colonies may "sponge up" more water; or (3) cells in S type colonies may secrete a greater mass of extracellular matrix. When disrupted and filtered, S type colonies yielded approximately ten times as many CFU/colony as R type colonies put through the same procedure. This greater yield of CFU from S colonies could be due to a combination of more cells being in the heavier colony and/or a greater adherence of cells in R type colonies.

Figure 7:
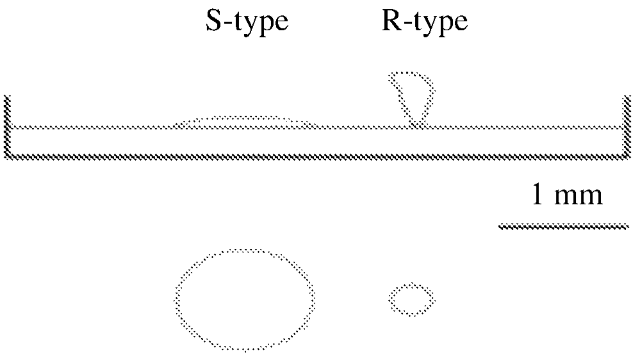
FIG. 7 is a cartoon representation of 10-day old R- and S-type colonies of Mtb ΔRD1 and shows the distinct morphologies of R- and S-type colonies viewed from the side (top panel) and the top (bottom panel).

Rough colonies appear hydrophobic, as if they are avoiding contact with the hydrated agar surface. Spread colonies seem to maximize contact with the agar. FIG. 7 shows a cartoon representation of 10-day old colonies of Mtb ΔRD1 viewed from the side (top panel) and from the top (bottom panel) of an agar plate. Many mycobacterial strains and species yielded colonies of the S morphotype when 0.05% Tween was in the medium, consistent with the detergent's emulsifying effect ameliorating a hydrophobicity of the R morphotype. On the other hand, tyloxapol which is also an emulsifying agent did not alter colony morphotypes of H37Rv ΔRD1. Raised colonies displayed a pattern of gene expression characteristic of microaerophyllic conditions in which the DosR regulon and other hypoxia-associated genes were upregulated. Spread colonies expressed genes characteristic of aerobic growth.

Despite the high rate of switching when colonies were grown from single cells, sectored colonies were never seen. The stress of single-cell isolation may allow cells to switch their morphotype but the decision is soon locked in.

Phase variation associated with visible colony morphology has been shown to be important for the colonization and pathogenic processes of other bacteria including *Pneumococcus, Staphylococcus*, and *Pseudomonas*. Related phenomena of semi-programmed antigenic variation occur in fungal and protozoan infections. Hypotheses concerning the role(s) of phase variation in the transmission and pathogenesis of *M. tuberculosis* will be of special interest for future work. This work has shown mycobacterial phase variation as formal genetics, i.e., a property of inheritance. The molecular mechanism(s) as well as the molecular outcomes of the process are now ripe for experimental attack. Phase variation in other systems can either be "cell autonomous," i.e., the phenotype of each cell is independent of other cells, or it can be an emergent property of microbial populations. The rate of phase variation in this study is high upon the shock of colony disruption but the lack of colony sectoring is evidence that once committed the phase state is stable. One speculation is that phase variation is coupled to the asymmetric cell division of the mycobacterial cell that initiates a colony. Another possibility is that quorum sensing represses switching during colony formation and is released by dilution upon colony disruption. A third possible mechanism is that R and S morphotypes are consequent to prion-like heredity of conformers in the bacterial extracellular matrix. The rate of phase variation in isolated cells of mycobacteria is high but not unprecedented. For example homothallic switching in appropriate yeast strains occurs every, or every other, cell generation). It would be a mistake to jump to the conclusion that the rapid and reversible process must be epigenetic. "Epigenetic" is a term often used imprecisely hut in almost all usages it means heredity that does not involve changes in primary DNA sequence. Epigenetics and phase variation are orthogonal concepts because some molecular mechanisms of phase variation are epigenetic whereas others involve changes in DNA sequence.

Example 2

Mtb is a pathogen estimated to have infected one third of the world population and killed 1.5 million people in 2013 (WHO 2013). Robert Koch demonstrated that Mtb was the causative agent for human tuberculosis in 1882 (Koch 1982). However, TB remains one of the deadliest infectious diseases, which is believed to be due to a large population of latently infected people serving as a reservoir for spreading the disease to new patients (Behr 1999; Tufariello 2003).

Figure 8:
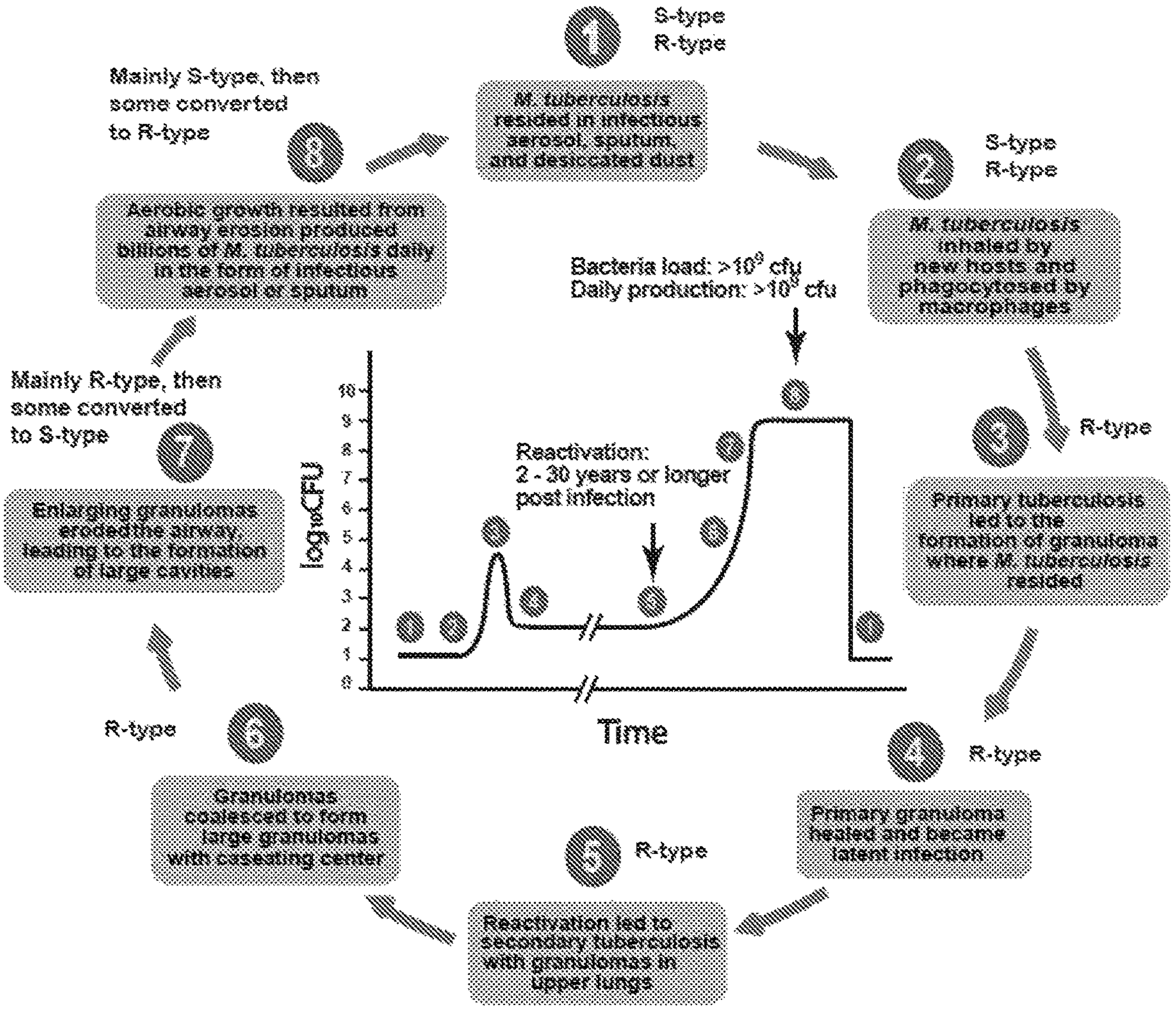
FIG. 8 shows a proposed disease cycle of human tuberculosis. Tuberculosis begins with *M. tuberculosis* (1) infectious aerosol, sputum, or desiccated dust (2) inhaled by new hosts and phagocytosed by macrophages (3) residing in granulomas resulting from primary tuberculosis, continues with (4) development of latent infection for 30 years or more, (5) reactivation to secondary tuberculosis, which leads to formation of granulomas in the upper lungs, (6) formation of coalesced granuloma with caseating center and (7) enlargement of granulomas into the airway leading to the formation of a cavity; (8) continuous aerobic growth resulting from airway invasion produces billions of *M. tuberculosis* daily contributing mightily to aerosol and sputum. This model is consistent with the following observations: (1) the population of tubercle bacilli in the cavity of an active tuberculosis patient can reach $10^9$ colony forming units (cfu), (2) a large number of tubercle bacilli estimated to range from $1.5\times10^9$ to $4.3\times10^9$ cfu were produced in an active TB patient in 24 hours, (3) sputum treated with sodium hydroxide directly spread on agar gave rise to colonies of two distinct morphotypes, S and R, and the antibiotic-killing kinetics of primary sputum *M. tuberculosis* are consistent with there being two populations of bacteria that differ in sensitivity, (4) findings that R and S morphotypes can switch when they are spread as single cells, (5) microarray analysis of the expression profile of R-type colonies pointed to their readiness for intracellular (hypoxic) growth, (6)S-type colonies grew twice as fast compared to R-type colonies on aerated 7H10 agar plates, and (7) R-type colonies seem to be more hydrophobic. The disease cycle includes both the growth of *M. tuberculosis* within an individual and its contagion from one person to another.

FIG. 8 is a proposed disease cycle of human TB including both Mtb growth within an individual and its contagion from one person to another (Russell 2011; Ernst 2012). In this model, it is hypothesized that the colony variants of S- and R-type are epigenetic states that are pre-adapted for success in different niches and/or to function in a complementary fashion. This model of states of Mtb optimized for different niches is consistent with the following observations: (1) sputum treated with sodium hydroxide directly spread on agar gave rise to colonies of two distinct morphotypes—smooth and rough (Petroff 1930); (2) nonlinear mixed-effects analysis of serial sputum colony counting data supports the existence of two bacillary subpopulations in sputum (Davies 2006); (3) the population of tubercle bacilli in the oxygen-rich lung cavity of active disease can reach 107 to 109 colony forming units (cfu), while those in the hypoxic caseous granuloma do not exceed 102 to 104 (Canetti 1955; Palaci 2007); (4) Mtb load and daily production is elevated five-fold in cavitary patients (Palaci 2007) and it has been estimated that daily production of 109 bacilli in patients with active TB (Osler 1892); (5) the findings disclosed herein that the R and S morphotypes can switch when they are spread as single cells; (6) the findings disclosed herein of microarray analysis of the expression profile of R-type colonies pointed to their readiness for intracellular hypoxic growth; and (7) the findings disclosed herein that S-type colonies, which it is hypothesized grow favorably in the lung cavity, grew 2-3 times faster in aerobic conditions than R-type colonies on 7H10 agar plates, consistent with the observations made by others (Yuan 1998). Therefore, it is hypothesized that S- and R-type phase variants are adapted to aerobic and hypoxic niches, respectively, and may also function in a complementary fashion in manipulating the host immune response.

Rapid and accurate diagnosis of TB is critical to the treatment of patients suspected of TB infection and the prevention of the spread of the disease (Davies 2008). However, TB diagnosis is often difficult due to factors that complicate the interpretation of the test results. Complicating factors include: (1) failure to differentiate active TB infection from latent TB infection (LTBI) (Menzies 2007; Pai, Zwerling 2008; Sester 2011); (2) failure to differentiate recent TB exposure from BCG vaccination (Lalvani 2001; Farhat 2006; Diel 2008); (3) presence of environmental NTM and the pulmonary infection caused by NTM (Katoch 2004; Wallace Jr. 2012); (4) difficulty in TB diagnosis due to the paucibacillary disease in children and immunocompromised patients (American 2000; Getahun 2007; Cattamanchi 2011); (5) difficulty in the diagnosis of extra-pulmonary TB (Chakravorty 2005; WHO 2007); and (6) failure to predict active TB disease in LTBI (Mazurek 2005; Andersen 2007; Diel 2008). Significant advancement in the development of improved TB diagnostic tools based on molecular (DNA), immunology, and culture has been fruitful in recent years; however, all of these advancements have suffered from downsides, including being time-consuming, having low sensitivity, having low specificity, cross-reacting to BCG vaccination and/or requiring expensive instrumentation and trained personnel (Pai 2015a; Pai 2015b). Therefore, there is a need to develop diagnostic tools that are rapid, sensitive, specific, cost-effective, and which can be deployed in community point-of-care clinics (Corbett 2003; Gandhi 2006).

When single cell suspensions were prepared by passing liquid cultures of *Mycobacterium tuberculosis* H37Rv (Mtb) through 5 μm filters, diluted and spread on 7H10 agar plates supplemented with OADC for slow growing mycobacteria, while only S-type colonies were observed for wild type Mtb (FIG. 2B, magnified as in FIG. 2E), it was observed that Mtb ΔRD1 (Hsu 2003) formed two distinct colony morphotypes, spread or smooth (S-type) and raised or rough (R-type) (FIG. 2B: arrow indicates R-type, magnified as in FIG. 2F at week 4 and FIG. 2G at week 8). Both S- and R-type Mtb ΔRD1 carried the RD1 deletion in Mtb genome, as demonstrated by DNA hybridization (FIG. 2D). Mtb ΔRD1 complemented with RD1 gave rise to S-type colonies on 7H10 agar (FIG. 2C). Surprisingly, as demonstrated in FIGS. 3A and 3B, Mtb ΔRD1 displayed property of phase variation when single cell suspensions of liquid culture derived from either S-type or R-type colonies produced both S-type (>80%) and R-type (<20%) colonies on 7H10 agar plates despite the parental colony type, while wild type Mtb produced only S-type colonies on agar plates supplemented with or without Tween 80. However, the true phase conversion rates for S- and R-type colonies (phase variants) were determined to be roughly 50% by spreading single cell suspensions prepared by passing PBS-suspended S- and R-type colonies of Mtb ΔRD1 ΔpanCD on 7H10 agar plates (data not shown). At first, it was not clear if the differential colony morphotypes of Mtb ΔRD1 were due to the RD1 deletion since R-type colony can be converted to S-type when the deletion strain was complemented with a copy of RD1 sequence wild type Mtb at the attB site in the chromosome. However, the two distinct morphotypes were also observed when many other defined null deletions were introduced into Mtb (Jain 2014). It was found that other mycobacterial strains and species also exhibited phase variation including *M. bovis* BCG Pasteur (BCG) and *M. smegmatis* mc2155 (Snapper 1990). Therefore, we determined that phase variation was not due to the loss of functions in RD1. Transcriptional analysis revealed distinct expression profiles in S-type versus R-type colonies. Genes most up-regulated in R-type were also induced in hypoxic culture belonging to the DosR regulon (Table 2). It was also observed that when colonies were young (10 days old), the R-type colonies appeared to grow upward and away from the surface of 7H10 agar plate while S-type colony grew outward and spread on the surface of 7H10 agar plate (FIG. 7). Although not wishing to be bound by any particular theory, it was hypothesized that R-type colonies had a hydrophobic surface, while S-type colonies had a hydrophilic surface. It is further hypothesized that S-type and R-type are adapted to aerobic (in lung cavities) and hypoxic (inside macrophages in granulomas) niches, respectively. According to our model, while latent-state Mtb resides inside hypoxic granulomas, Mtb must alter its transcriptional profile for aerobic growth in cavities after re-activation. S-type colony, which is hypothesized to grow favorably in the lung cavities, grew 2-3 times faster in aerobic conditions than the R-type colony on 7H10 agar plate (based on colony weight). It is advantageous for Mtb in the lung cavities to grow as S-type phase variant in order to produce large amounts of contagions which will be spread to the ex vivo environment through coughing and the production of phlegm. On the contrary, it is advantageous for some S-type Mtb to convert to R-type phase variants before infecting new patients where R-type will be phagocytosed by macrophages into hypoxic phagosomes. It is therefore logical to postulate that S- and R-type phase variants may function in a complementary fashion in manipulating the immune response as S-type phase variants are likely to be destroyed and the associated antigens are presented to the host immune system. Mtb ΔRD1 ΔpanCD, a BSL-2 level attenuated mycobacteria, will be used throughout the proposed studies (Sambandamurthy 2006). Mtb ΔRD1 panCD exhibited phase variation similar to its parent strain, Mtb ΔRD1.

Enrichment of Phase-Specific Immunogens for the Production of Phase-Specific mAbs:

In order to develop phase-specific mAbs against Mtb, phase specific immunogens will be enriched according to a modified two-step protocol described previously (Takeda 2008). The first step is to immunize 5 Balb/c mice with immunogens prepared from S-type colony (S-type immunogens). The polyclonal antibodies reacting to S-type immunogens (S-type sera) will be pooled, and mixed with the immunogens prepared from the R-type phase variant (R-type immunogens) and subjected to immunoprecipitation to enrich the R-type-specific immunogens. The enrichment will be repeated two to three times using the fresh S-type sera. Further enrichments will be performed using immune sera specific to non-tuberculosis mycobacteria. The enriched R-type immunogens will be used to immunize naïve Balb/c mice (homogenized with Incomplete Freund's Adjuvant) for the production of R-type phase variant specific hybridomas and mAbs. The enrichment process will be repeated for S-type immunogens for the production of S-type phase variant-specific hybridomas and mAbs.

Fusion with NSO Myeloma Cells:

Five (5) Balb/c mice (6-8 weeks old) will be immunized subcutaneously with enriched R-type immunogens described. Mice will be sacrificed three-month after the first immunization, and total spleen cells will be obtained according to a procedure described previously (Reeves 2001). Cells will be treated for 48 hours with 50 μg/ml lipopolysaccharide (LPS, *E. coli,* 055:B5; Sigma) and 25 ng/ml interleukin-4 (IL-4, murine recombinant; R & D) in DMEM containing 20% fetal calf serum, 1% sodium pyruvate, 1% non-essential amino acids, penicillin and gentamicin. Forty-eight hours post-treatment, the spleen cells (estimated to have $2.4\times10^7$ B cells in total) will be washed in DMEM three times, and allowed to fuse with $8\times10^6$ NSO myeloma cells (B cell to myeloma cell ratio=3:1) (Groth 1980). The NSO myeloma cell line has been reported (Ray 1994). Hybrids will be screened for binding with Mtb ΔRD1 ΔpanCD antigens comprising whole cell lysates. Positive wells will be cloned by growing on soft agarose plates. Quantitation of monoclonal antibodies (mAbs) from hybridoma supernatants will be determined by ELISA. The supernatants containing mAbs will be subjected to further analysis upon normalization of concentrations of immunoglobulins.

Screening of mAb Production Hybridomas by ELISA:

Wells of 96-well microtiter plates will be coated with 50 μl of antigenic mixtures (15 ng/μ1) comprising whole cell lysates of Mtb ΔRD1 ΔpanCD phase variants in phosphate-buffered saline (PBS, pH 7.2) at 4° C. overnight; blocked with 50 μl of 1% bovine serum albumin (BSA) in PBS at room temperature (RT) for 2 hours and subsequently washed thrice with 0.05% Tween 20 in PBS. Twenty-five (25) μl of the appropriate hybridoma cell supernatants containing mAbs will be added, in triplicates, to react with an antigen-coated well at 40 C overnight. Wells will be washed three times before the addition of 25 μl of goat anti-mouse alkaline phosphatase-conjugated antibody. One hour later at 37° C., wells will be washed five times, and 50 μl of 1 mg/ml p-nitrophenylphosphate in substrate buffer will be added to each well, and the plates developed at RT. The absorbance at 405 nm of wells will be measured using a microplate reader (Dynex), and the optical densities derived from triplicate wells will be averaged. Negative controls consist of wells in which PBS was added in lieu of hybridoma supernatants. Positive controls will use the mouse mAb CS-49 (IgG1) and CS-50 (IgA) that recognize the immune-dominant Mtb protein α-crystallin, detectable in patients with active TB.

Microscopy Examination of Sputum Smear Prepared from Patients with Active TB Infection:

The mAbs developed will be used to differentially stain the phase variants and various strains of mycobacteria, including wild type Mtb, BCG, *M. smegmatis*, and other NTM that have been implicated in patients suspected of active TB. mAbs that are specific to Mtb phase variants will be tested using sputum smear prepared from patients with active pulmonary TB. According to standard protocol, unused sputum samples will be stored at −80° C. for the proposed study. IHC staining on these sputum smear samples will be double-blinded to protect the privacy of the patients. The acid-fast staining for each sputum smear tested will be used as a control.

It is expected these experiments will identify mAbs that specifically react to each phase variant of Mtb, but not NTM. These mAbs can be used to differentially stain S- and R-type variants of Mtb prepared from Mtb culture by IHC. It is expected that there will be S-type phase variants alongside R-type phase variants in sputum prepared from patients with active TB. Example 3.

Determine the Differential Surface Hydrophobicity of Mycobacteria Exhibit Phase Variation:

Colony of each phase variant will be collected into PBS and prepared into cell suspension by passing through 28-gauge needle (Stokes 2004). The relative hydrophobicity index of each phase variant of Mtb ΔRD1 panCD will be determined according to the hexadecane partition method (Rosenberg 1980). Optical density of each sample will be adjusted and normalized before the measurement of hydrophobicity. Equal volumes of reagents will be added to single cell suspensions in glass culture tubes, shaken vigorously for 2 minutes, then allowed to partition aqueous and organic phases. Optical density of the aqueous phase will be determined and used to calculate the relative hydrophobicity index which is defined as the percent reduction of reading at $O.D._{650}$.

Determine the Surface Chemical Properties of Mtb Phase Variants:

To begin to understand the complex nature of the cell wall structure of Mtb, the differential expression of lipid components will be analyzed by thin-layer chromatography (TLC). Colonies of each phase variant of Mtb ΔRD1 ΔpanCD grown to 4-weeks old will be collected for total lipid extraction (Morita 2005). Lipids extracted will be separated by 2-D TLC according to a procedure described previously (Besra 1998). Different solvent systems will be employed to resolve major lipid species present on Mtb surface including phthiocerol dimycocerosate, sulfolipids, glycolipids such as trehalose dimycolate, lipooligosaccharides, and phospholipids such as phosphatidylinositol mannosides. For any differential expression of lipid species recognized by TLC, the lipid will be purified from the TLC plate and analyzed by mass spectrometry to identify the nature of the lipid. It has been noted that the transcriptional profile of the R-type colonies appears similar to the transcriptional profile of Mtb grown as a pellicle, including the up-regulation of dosR regulon, heat shock proteins, sigma factors such as sigB and sigE, icl and pckA (Table 2). Because pellicles of Mtb are known to be up-regulated in papA3 involved in the biosynthesis of pentaacyl trehaloses, papA1 involved in sulfolipid biosynthesis, it is expected that these lipids are the potential lipids that are up-regulated in the rough morphotype.

Comparative Proteomic Analysis of Mtb Phase Variants:

Isobaric labeling multiplexed quantitative proteomics will be used to study differential proteomics of S- and R-type phase variants of Mtb. Briefly, three colonies of each phase variant of Mtb ΔRD1 ΔpanCD will be identified and collected into conical tubes and prepared into cell-free extract by passing the samples through French Press. The concentration of each sample will be normalized and adjusted to 1 mg/ml, labeled with isobaric tagging reagent (Rauniyar 2014) (Thermo Fisher Scientific TMT 6-plex), and then pooled into one mixed sample. The sample will be pre-fractionated using high pH reversed phase chromatography (Yang 2012); the fractions will be concatenated and combined to generate 12 fractions for online nanoLC-MS/MS. The experiment with two total protein extracts prepared from S- and R-type phase variants will be repeated with isobaric labeling in reverse to validate the experimental data and to serve as controls. Differentially expressed proteins will be identified and the roles of these proteins determined biochemically, bioinformationally, and genetically by constructing and studying defined deletion mutants with and without complementation (Jain 2014).

It is expected that there will be a difference in hydrophobicity of the S- and R-type phase variants of Mb, and that this difference will be compromised by the addition of Tween 80 to the agar plates. It is expected that there are variations in the lipid composition of the two colony morphotypes.

REFERENCES

Cheng N, Porter M A, Frick L W, Nguyen Y, Hayden J D, Young E F, Braunstein M S, Hull-Ryde E A, Janzen W P. 2014. Filtration improves the performance of a high-throughput screen for anti-mycobacterial compounds. PLoS One 9:e96348.

Avery O T, MacLeod C M, McCarty M. 1944. Studies on the chemical nature of the substance inducing transformation of pneumococcal types induction of transformation by a desoxyribonucleic acid fraction isolated from pneumococcus type III. The Journal of experimental medicine 79:137-158.

Koch R. 1967. Nobel Lectures, Physiology or Medicine 1901-1921. Elsevier Publishing Company, Amsterdam.

Petroff S A. 1927. Microbic Dissociation The Tubercle *Bacillus*. Experimental Biology and Medicine 24:632-634.

Petroff S A, Steenken W. 1930. Biological studies of the tubercle *bacillus* I. Instability of the organism and microbic dissociation. The Journal of experimental medicine 51:831-845.

Steenken Jr W, Oatway Jr W H, Petroff S A. 1934. Biological studies of the tubercle *bacillus*: III. Dissociation and pathogenicity of the R and S variants of the human tubercle *bacillus* (H37). The Journal of experimental medicine 60:515.

Andreu N, Gibert I. 2008. Cell population heterogeneity in *Mycobacterium tuberculosis H*37Rv. Tuberculosis 88:553-559.

Fujiwara N, Ohara N, Ogawa M, Maeda S, Naka T, Taniguchi H, Yamamoto S, Ayata M. 2015. Glycopeptidolipid of *Mycobacterium smegmatis* J15cs Affects Morphology and Survival in Host Cells. PloS one 10:e0126813.

Proctor R A, Von Eiff C, Kahl B C, Becker K, McNamara P, Herrmann M, Peters G. 2006. Small colony variants: a pathogenic form of bacteria that facilitates persistent and recurrent infections. Nature Reviews Microbiology 4:295-305.

Ruger K, Hampel A, Billig S, RÃ¼cker N, Suerbaum S, Bange F-C. 2014. Characterization of Rough and Smooth Morphotypes of *Mycobacterium abscessus* Isolates from Clinical Specimens. Journal of clinical microbiology 52:244-250.

Supply P, Marceau M, Mangenot S, Roche D, Rouanet C, Khanna V, Majlessi L, Criscuolo A, Tap J, Pawlik A. 2013. Genomic analysis of smooth tubercle bacilli provides insights into ancestry and pathoadaptation of *Mycobacterium tuberculosis*. Nature genetics 45:172-179.

Sousa A M, Machado I, Nicolau A, Pereira M O. 2013. Improvements on colony morphology identification towards bacterial profiling. Journal of microbiological methods 95:327-335.

Sousa A M, Pereira M O, Lourenco A. 2015. MorphoCol: An ontology-based knowledgebase for the characterisation of clinically significant bacterial colony morphologies. Journal of biomedical informatics 55:55-63.

Novick A, Weiner M. 1957. Enzyme induction as an all-or-none phenomenon. Proc Nat Acad Sci usa 43:553-566.

Dylan B. 1965. "You know something is happening but you don't know what it is" from: 'Ballad of a thin man', track 5, Highway 61 Revisited, Columbia Records New York, N.Y.

Lederberg J, lino T. 1956. Phase variation in *Salmonella*. Genetics 41:743.

Dubos R J. 1945. The bacterial cell in relation to problems of virulence, immunity and chemotherapy. Harvard University Press.

Lederberg J. 1948. Problems in microbial genetics. Heredity 2:145-198.

Dubos R J, Middlebrook G. 1947. Media for tubercle bacilli. American Review of Tuberculosis and Pulmonary Diseases 56:334-345.

Larsen M H, Biermann K, Tandberg S, Hsu T, Jacobs W R. 2007. Genetic manipulation of *Mycobacterium tuberculosis*. Current protocols in microbiology:10A. 12.11-10A. 12.21.

Middlebrook G, Dubos R J, Pierce C. 1947. Virulence and morphological characteristics of mammalian tubercle bacilli. The Journal of experimental medicine 86:175-184.

Hsu T, Hingley-Wilson S M, Chen B, Chen M, Dai A Z, Morin P M, Marks C B, Padiyar J, Goulding C, Gingery M. 2003. The primary mechanism of attenuation of *bacillus* Calmette-Guerin is a loss of secreted lytic function required for invasion of lung interstitial tissue. Proceedings of the National Academy of Sciences 100:12420-12425.

Sambandamurthy V K, Derrick S C, Hsu T, Chen B, Larsen M H, Jalapathy K V, Chen M, Kim J, Porcelli S A, Chan J. 2006. *Mycobacterium tuberculosis* DRD1 DpanCD: a safe and limited replicating mutant strain that protects immunocompetent and immunocompromised mice against experimental tuberculosis. Vaccine 24:6309-6320.

Green M, Sambrook J. 2012. Molecular cloning: A laboratory manual. New York: Cold Spring Harbor Laboratory. (Fourth Edition). (Cold Spring Harbor Press, Plainview, N.Y.).

Jain P, Hsu T, Arai M, Biermann K, Thaler D S, Nguyen A, GonzÃ¡lez P A, Tufariello J M, Kriakov J, Chen B. 2014. Specialized transduction designed for precise high-throughput unmarked deletions in *Mycobacterium tuberculosis*. MBio 5:e01245-01214.

Jain P, Weinrick B, Kalivoda E, Yang H, Munsamy V, Vilcheze C, Weisbrod T, Larsen M, O'Donnell M, Pym A, Jacobs W J. 2016. Dual-Reporter Mycobacteriophages (Phage2 DRMs) Reveal Preexisting *Mycobacterium tuberculosis* Persistent Cells in Human Sputum. MBio 7:e01023-01016.

Ioerger T R, Feng Y, Ganesula K, Chen X, Dobos K M, Fortune S, Jacobs W R, Mizrahi V, Parish T, Rubin E. 2010. Variation among genome sequences of H37Rv strains of *Mycobacterium tuberculosis* from multiple laboratories. Journal of bacteriology 192:3645-3653.

Jacobs W J, Hsu T, Bardarov S, Bardarov S. 2010. Attenuated *Mycobacterium Tuberculosis Vaccines U.S. Pat. No.* 7,722,861 B2.

Manso A S, Chai M H, Atack J M, Furi L, Croix M D S, Haigh R, Trappetti C, Ogunniyi A D, Shewell L K, Boitano M. 2014. A random six-phase switch regulates pneumococcal virulence via global epigenetic changes. Nature communications 5.

Brooks J L, Jefferson K K. 2014. Phase variation of poly-N-acetylglucosamine expression in *Staphylococcus aureus*. PLoS Pathog 10:e1004292.

Achouak W, Conrod S, Cohen V, Heulin T. 2004. Phenotypic variation of *Pseudomonas brassicacearum* as a plant root-colonization strategy. Molecular plant-microbe interactions 17:872-879.

Deitsch K W, Lukehart S A, Stringer J R. 2009. Common strategies for antigenic variation by bacterial, fungal and protozoan pathogens. Nat Rev Microbiol 7:493-503.

Ptashne M. 1986. A genetic switch: Gene control and phage. lambda.

Chia N, Woese C R, Goldenfeld N. 2008. A collective mechanism for phase variation in biofilms. Proceedings of the National Academy of Sciences 105:14597-14602.

McClintock B. 1983. The significance of responses of the genome to challenge. Science 226:792-801.

Hayashi J M, Luo C Y, Mayfield J A, Hsu T, Fukuda T, Walfield A L, Giffen S R, Leszyk J D, Baer C E, Bennion O T, Madduri A, Shaffer S A, Aldridge B B, Sassetti C M, Sandler S J, Kinoshita T, Moody D B, Morita Y S. 2016. Spatially distinct and metabolically active membrane domain in mycobacteria. Proc Natl Acad Sci USA doi: 10.1073/pnas.1525165113.

Santi I, Dhar N, Bousbaine D, Wakamoto Y, McKinney J D. 2013. Single-cell dynamics of the chromosome replication and cell division cycles in mycobacteria. Nat Commun 4:2470.

Nadell C D, Drescher K, Foster K R. 2016. Spatial structure, cooperation and competition in biofilms. Nat Rev Microbiol 14:589-600.

Thaler D S. 2009. The cytoplasmic structure hypothesis for ribosome assembly, vertical inheritance, and phylogeny. Bioessays 31:774-783.

Dalgaard J Z, Klar A J. 1999. Orientation of DNA replication establishes mating-type switching pattern in *S. pombe*. Nature 400:181-184.

Sapp J. 2016. Epigenetics and Beyond. In Matlin K (ed), Visions of Cell Biology. University of Chicago Press, Chicago, Ill.

Field D, Magnasco M O, Moxon E R, Metzgar D, Tanaka M M, Wills C, Thaler D S. 1999. Contingency loci, mutator alleles, and their interactions. Synergistic strategies for microbial evolution and adaptation in pathogenesis. Ann N Y Acad Sci 870:378-382.

Moxon E R, Thaler D S. 1997. The tinkerer's evolving toolbox. Nature 387:659-662.

Pym A S, Brodin P, Brosch R, Huerre M, Cole S T. 2002. Loss of RD1 contributed to the attenuation of the live tuberculosis vaccines *Mycobacterium bovis* BCG and *Mycobacterium microti*. Molecular microbiology 46:709-717.

Seth V, Kabra S K. 2006. Essentials of tuberculosis in children. JAYPEE BROTHERS PUBLISHERS.

Jindani A, Aber V R, Edwards E A, Mitchison D A. 1980. The Early Bactericidal Activity of Drugs in Patients with Pulmonary Tuberculosis 1, 2. American Review of Respiratory Disease 121:939-949.

Osler W. 1892. Tuberculosis. In: The Principles and Practice of Medicine. Appleton, N.Y.

Davies G R, Brindle R, Khoo S H, Aarons L J. 2006. Use of nonlinear mixed-effects analysis for improved precision of early pharmacodynamic measures in tuberculosis treatment. Antimicrob Agents Chemother 50:3154-3156.

Cambier C J, Takaki K K, Larson R P, Hernandez R E, Tobin D M, Urdahl K B, Cosma C L, Ramakrishnan L. 2014. Mycobacteria manipulate macrophage recruitment through coordinated use of membrane lipids. Nature 505:218-222.

Neyrolles O, Guilhot C. 2011. Recent advances in deciphering the contribution of *Mycobacterium tuberculosis* lipids to pathogenesis. Tuberculosis 91:187-195.

Klepp L I, Forrellad M A, Osella A V, Blanco F C, Stella E J, Bianco MVn, de la Paz Santangelo M, Sassetti C, Jackson M, Cataldi A A. 2012. Impact of the deletion of the six mce operons in *Mycobacterium smegmatis*. Microbes and Infection 14:590-599.

Lemassu A, Ortalo-Magne A, Bardou F, Silve G, Laneelle M A, Daffe M. 1996. Extracellular and surface-exposed polysaccharides of non-tuberculous mycobacteria. Microbiology 142 (Pt 6):1513-1520.

Steenken Jr W, Gardner L U. 1946. History of H37 strain of tubercle *bacillus*. American review of tuberculosis 54:62-66.

Larsen M H, Biermann K, Chen B, Hsu T, Sambandamurthy V K, Lackner A A, Aye P P, Didier P, Huang D, Shao L. 2009. Efficacy and safety of live attenuated persistent and rapidly cleared *Mycobacterium tuberculosis* vaccine candidates in non-human primates. Vaccine 27:4709-4717.

Vilcheze C, Hartman T, Weinrick B, Jacobs Jr W R. 2013. *Mycobacterium tuberculosis* is extraordinarily sensitive to killing by a vitamin C-induced Fenton reaction. Nature communications 4.

Snapper S B, Melton R E, Mustafa S, Kieser T, Wr Jr J. 1990. Isolation and characterization of efficient plasmid transformation mutants of *Mycobacterium smegmatis*. Molecular microbiology 4:1911-1919.

American Thoracic Society. (2000). "Diagnostic standards and classification of tuberculosis in adults and children." Am J Respir Crit Care Med 161: 1376-1395.

Andersen, P., Doherty, T. M., Pai, M. and Weldingh, K. (2007). "The prognosis of latent tuberculosis: can disease be predicted?" Trends in molecular medicine 13(5): 175-182.

Behr, M. A., Warren, S. A., Salamon, H., Hopewell, P. C., De Leon, A. P., Daley, C. L. and Small, P. M. (1999). "Transmission of *Mycobacterium tuberculosis* from patients smear-negative for acid-fast bacilli." The Lancet 353(9151): 444-449.

Besra, G. S. (1998). "Preparation of cell-wall fractions from mycobacteria." Mycobacteria protocols: 91-107.

Canetti, G. (1955). The tubercle *bacillus* in the pulmonary lesion of man: histobacteriology and its bearing on the therapy of pulmonary tuberculosis. New York, N.Y., Springer Verlag.

Cattamanchi, A., Smith, R., Steingart, K. R., Metcalfe, J. Z., Date, A., Coleman, C., Marston, B. J., Huang, L., Hopewell, P. C. and Pai, M. (2011). "Interferon-gamma release assays for the diagnosis of latent tuberculosis infection in HIV-infected individuals: a systematic review and meta-analysis." Journal of acquired immune deficiency syndromes (1999) 56(3): 230.

Chakravorty, S., Sen, M. K. and Tyagi, J. S. (2005). "Diagnosis of extrapulmonary tuberculosis by smear, culture, and PCR using universal sample processing technology." Journal of clinical microbiology 43(9): 4357-4362.

Corbett, E. L., Watt, C. J., Walker, N., Maher, D., Williams, B. G., Raviglione, M. C. and Dye, C. (2003). "The growing burden of tuberculosis: global trends and interactions with the HIV epidemic." Archives of internal medicine 163(9): 1009-1021.

Davies, P. D. O. and Pai, M. (2008). "The diagnosis and misdiagnosis of tuberculosis [State of the art series. Tuberculosis. Edited by I D Rusen. Number 1 in the series]." The International Journal of Tuberculosis and Lung Disease 12(11): 1226-1234.

Diel, R., Loddenkemper, R., Meywald-Walter, K., Niemann, S. and Nienhaus, A. (2008). "Predictive value of a whole blood IFN-Î³ assay for the development of active tuberculosis disease after recent infection with *Mycobacterium tuberculosis*." American journal of respiratory and critical care medicine 177(10): 1164-1170.

Ernst, J. D. (2012). "The immunological life cycle of tuberculosis." Nat Rev Immunol 12(8): 581-91.

Farhat, M., Greenaway, C., Pai, M. and Menzies, D. (2006). "False-positive tuberculin skin tests: what is the absolute effect of BCG and non-tuberculous mycobacteria? [Review Article]." The International Journal of Tuberculosis and Lung Disease 10(11): 1192-1204.

Gandhi, N. R., Moll, A., Sturm, A. W., Pawinski, R., Govender, T., Lalloo, U., Zeller, K., Andrews, J. and Friedland, G. (2006). "Extensively drug-resistant tuberculosis as a cause of death in patients co-infected with tuberculosis and HIV in a rural area of South Africa." The Lancet 368(9547): 1575-1580.

Getahun, H., Harrington, M., O'Brien, R. and Nunn, P. (2007). "Diagnosis of smear-negative pulmonary tuberculosis in people with HIV infection or AIDS in resource-constrained settings: informing urgent policy changes." The Lancet 369(9578): 2042-2049.

Groth, S. F. d. S. and Scheidegger, D. (1980). "Production of monoclonal antibodies: strategy and tactics." Journal of immunological methods 35(1-2): 1-21.

Huebner, R. E., Schein, M. F. and Bass Jr, J. B. (1993). "The tuberculin skin test." Clinical Infectious Diseases: 968-975.

Katoch, V. M. (2004). "Infections due to non-tuberculous mycobacteria (NTM)." Indian Journal of Medical Research 120(4): 290.

Koch, R. (1982). "Classics in infectious diseases. The etiology of tuberculosis: Robert Koch. Berlin, Germany 1882." Rev Infect Dis 4(6): 1270-4.

Lalvani, A., Pathan, A. A., Durkan, H., Wilkinson, K. A., Whelan, A., Deeks, J. J., Reece, W. H. H., Latif, M., Pasvol, G. and Hill, A. V. S. (2001). "Enhanced contact tracing and spatial tracking of *Mycobacterium tuberculosis* infection by enumeration of antigen-specific T cells." The Lancet 357(9273): 2017-2021.

Mazurek, G. H., Jereb, J., LoBue, P., Iademarco, M. F., Metchock, B. and Vernon, A. (2005). "Guidelines for using the QuantiFERON-TB Gold test for detecting *Mycobacterium tuberculosis* infection, United States." MMWr recomm rep 54(RR-15): 49-55.

Menzies, D., Pai, M. and Comstock, G. (2007). "Meta-analysis: new tests for the diagnosis of latent tuberculosis infection: areas of uncertainty and recommendations for research." Annals of internal medicine 146(5): 340-354.

Morita, Y. S., Velasquez, R., Taig, E., Waller, R. F., Patterson, J. H., Tull, D., Williams, S. J., Billman-Jacobe, H. and McConville, M. J. (2005). "Compartmentalization of lipid biosynthesis in mycobacteria." J Biol Chem 280(22): 21645-52.

Pai, M. (2015a). "Innovations in Tuberculosis Diagnostics: Progress and Translational Challenges." EBioMedicine 2(3): 182-183.

Pai, M. and Schito, M. (2015b). "Tuberculosis diagnostics in 2015: landscape, priorities, needs, and prospects." Journal of Infectious Diseases 211(suppl 2): S21-S28.

Pai, M., Zwerling, A. and Menzies, D. (2008). "Systematic review: T-cell-based assays for the diagnosis of latent tuberculosis infection: an update." Annals of internal medicine 149(3): 177-184.

Palaci, M., Dietze, R., Hadad, D. J., Ribeiro, F. K., Peres, R. L., Vinhas, S. A., Maciel, E. L., do Valle Dettoni, V., Horter, L., Boom, W. H., Johnson, J. L., Eisenach, K. D. (2007). "Cavitary disease and quantitative sputum bacillary load in cases of pulmonary tuberculosis." J Clin Microbiol 45(12): 4064-6.

Rauniyar, N. and Yates Iii, J. R. (2014). "Isobaric labeling-based relative quantification in shotgun proteomics." Journal of proteome research 13(12): 5293-5309.

Raviglione, M. and Director, G. T. B. (2013). Global strategy and targets for tuberculosis prevention, care and control after 2015, Geneva, World Health Organization.

Ray, S. and Diamond, B. (1994). "Generation of a fusion partner to sample the repertoire of splenic B cells destined for apoptosis." Proceedings of the National Academy of Sciences 91(12): 5548-5551.

Reeves, J. and Reeves, P. (2001). "Removal of Lymphoid Organs." Current protocols in immunology: 1.9.1-1.9.3.

Robertson, D., Savage, K., Reis-Filho, J. S. and Isacke, C. M. (2008). "Multiple immunofluorescence labelling of formalin-fixed paraffin-embedded (FFPE) tissue." BMC cell biology 9(1): 1.

Rosenberg, M., Gutnick, D. and Rosenberg, E. (1980). "Adherence of bacteria to hydrocarbons: a simple method for measuring cell-surface hydrophobicity." FEMS Microbiology letters 9(1): 29-33.

Russell, D. G. (2011). "*Mycobacterium tuberculosis* and the intimate discourse of a chronic infection." Immunol Rev 240(1): 252-68.

Sester, M., Sotgiu, G., Lange, C., Giehl, C., Girardi, E., Migliori, G. B., Bossink, A., Dheda, K., Diel, R. and Dominguez, J. (2011). "Interferon-g release assays for the diagnosis of active tuberculosis: a systematic review and meta-analysis." European Respiratory Journal 37(1): 100-111.

Steingart, K. R., Henry, M., Ng, V., Hopewell, P. C., Ramsay, A., Cunningham, J., Urbanczik, R., Perkins, M., Aziz, M. A. and Pai, M. (2006). "Fluorescence versus conventional sputum smear microscopy for tuberculosis: a systematic review." The Lancet infectious diseases 6(9): 570-581.

Stokes, R. W., Norris-Jones, R., Brooks, D. E., Beveridge, T. J., Doxsee, D., Thorson, L. M. (2004). "The glycanrich outer layer of the cell wall of *Mycobacterium tuberculosis* acts as an antiphagocytic capsule limiting the association of the bacterium with macrophages." Infect Immun 72(10): 5676-86.

Takeda, K., Watanabe, C., Qadota, H., Hanazawa, M. and Sugimoto, A. (2008). "Efficient production of monoclonal antibodies recognizing specific structures in *Caenorhabditis elegans* embryos using an antigen subtraction method." Genes to Cells 13(7): 653-665.

Tufariello, J. M., Chan, J., Flynn, J. L. (2003). "Latent tuberculosis: mechanisms of host and *bacillus* that contribute to persistent infection." Lancet Infect Dis 3(9): 578-90.

Ulrichs, T., Lefmann, M., Reich, M., Morawietz, L., Roth, A., Brinkmann, V., Kosmiadi, G. A., Seiler, P., Aichele, P., Hahn, H., Krenn, V., Gobel, U. B., Kaufmann, S. H. (2005). "Modified immunohistological staining allows detection of Ziehl-Neelsen-negative *Mycobacterium tuberculosis* organisms and their precise localization in human tissue." J Pathol 205(5): 633-40.

Wallace Jr, R. J., O'Brien, R., Glassroth, J., Raleigh, J. and Dutt, A. (2012). "Diagnosis and treatment of disease caused by nontuberculous mycobacteria." American Review of Respiratory Disease.

WHO. (2007). "Improving the diagnosis and treatment of smear-negative pulmonary and extrapulmonary tuberculosis among adults and adolescents: recommendations for HIV-prevalent and resource-constrained settings."

WHO. (2013). "Global tuberculosis report". Geneva, World Health Organization.

WHO. (2014). "High priority target product profiles for new tuberculosis diagnostics: report of a consensus meeting, 28-29 Apr. 2014, Geneva, Switzerland."

Yang, F., Shen, Y., Camp, D. G. and Smith, R. D. (2012). "High-pH reversed-phase chromatography with fraction concatenation for 2D proteomic analysis." Expert review of proteomics 9(2): 129-134.

Yuan, Y., Crane, D. D., Simpson, R. M., Zhu, Y. Q., Hickey, M. J., Sherman, D. R., Barry 3rd., C. E., (1998). "The 16-kDa alpha-crystallin (Acr) protein of *Mycobacterium tuberculosis* is required for growth in macrophages." Proc Natl Acad Sci USA 95(16): 9578-83.

Zogaj, X., Nimtz, M., Rohde, M., Bokranz, W. and Romling, U. (2001). "The multicellular morphotypes of *Salmonella typhimurium* and *Escherichia coli* produce cellulose as the second component of the extracellular matrix." Mol Microbiol 39(6): 1452-63.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for detecting a rough-type *mycobacterium* and a smooth-type *mycobacterium* in a sample, wherein the *mycobacterium* is *Mycobacterium tuberculosis* or *Mycobacterium bovis*, comprising:

providing a sample; and independently detecting the rough-type *mycobacterium* and the smooth-type *mycobacterium* in the sample, wherein:

detecting the rough-type *mycobacterium* comprises detecting universal stress protein family protein TB31.7; and detecting the smooth-type *mycobacterium* comprises (i) detecting a protein, lipid or polysaccharide preferentially expressed by the smooth-type *mycobacterium*, and not expressed by the rough-type *mycobacterium* to a measurable degree, (ii) detecting a molecule preferentially secreted by the smooth-type *mycobacterium*, and not secreted by the rough-type *mycobacterium* to a measurable degree, (iii) visually inspecting the surface of a colony of the *mycobacterium*, wherein a colony of *mycobacterium* whose surface is round in two dimensions and dome-shaped in three dimensions and lacks indentations or sharp angles is smooth-type, or (iv) detecting mRNA preferentially expressed by the smooth-type *mycobacterium*, and not expressed by the rough-type *mycobacterium* to a measurable degree, wherein detecting the smooth-type *mycobacterium* comprises visually inspecting the surface of a colony of the *mycobacterium*, wherein a colony of *mycobacterium* whose surface is round in two dimensions and dome-shaped in three dimensions and lacks indentations or sharp angles is smooth-type, thereby detecting the rough-type *mycobacterium* and the smooth-type *mycobacterium* in the sample.

2. The method of claim 1, wherein the sample is from a human.

3. The method of claim 1, wherein the sample is blood, sputum, phlegm, urine, or stool.

4. The method of claim 1, wherein detecting the smooth-type *mycobacterium* comprises detecting a protein, lipid or polysaccharide preferentially expressed by the smooth-type *mycobacterium.*

5. The method of claim 4, wherein detecting the smooth-type *mycobacterium* comprises detecting a lipid preferentially expressed by the smooth-type *mycobacterium.*

6. The method of claim 4, wherein detecting the smooth-type *mycobacterium* comprises detecting a polysaccharide preferentially expressed by the smooth-type *mycobacterium.*

7. The method of claim 4, wherein detecting the smooth-type *mycobacterium* comprises detecting a protein preferentially expressed by the smooth-type *mycobacterium.*

8. The method of claim 7, wherein the protein preferentially expressed by the smooth-type *mycobacterium* is molybdopterin biosynthesis protein (MoeA1), PE family protein PE13, zinc protease (PepR), 3-isopropylmalate dehydratase (LeuC), cholesterol oxidase (ChoD), D-amino acid oxidase (Aao), 3-oxoacyl-[acyl-carrier protein] reductase (FabG4), pyridoxamine 5'-phosphate oxidase (PNP/PMP oxidase) 23S rRNA methyltransferase (tsnR), 3-isopropylmalate dehydratase (LeuD), PE family protein PE25 or 4-diphosphocytidyl-2C-methyl-D-erythritol synthase IspD (MEP cytidyltransferase).

9. The method of claim 1, wherein detecting the smooth-type *mycobacterium* comprises detecting a molecule preferentially secreted by the smooth-type *mycobacterium.*

10. The method of claim 1, further comprising incubating the sample with a molecule that selectively binds to universal stress protein family protein TB31.7; and detecting the rough-type *mycobacterium* by detecting the molecule that selectively binds to universal stress protein family protein TB31.7.

11. The method of claim 1, further comprising incubating the sample with a molecule that selectively binds to a protein, lipid or polysaccharide preferentially expressed by the smooth-type *mycobacterium*; and detecting the smooth-type *mycobacterium* by detecting the molecule that selectively binds to a protein, lipid or polysaccharide preferentially expressed by the smooth-type *mycobacterium.*

12. The method of claim 1, further comprising incubating the sample with a second molecule that binds to a molecule preferentially secreted by the smooth-type *mycobacterium*; and detecting the smooth-type *mycobacterium* by detecting the second molecule.

13. The method of claim 10, wherein the molecule that selectively binds to universal stress protein family protein TB31.7 is a monoclonal antibody.

14. The method of claim 11, wherein the molecule that selectively binds to a protein, lipid or polysaccharide preferentially expressed by the smooth-type *mycobacterium* is a monoclonal antibody.

15. The method of claim 1, wherein detecting the rough-type *mycobacterium* further comprises visually inspecting the surface of a colony of the *mycobacterium*, wherein a colony of *mycobacterium* whose surface is irregular in shape in both two and three dimensions is rough-type.

16. The method of claim 1, wherein detecting the smooth-type *mycobacterium* comprises detecting mRNA preferentially expressed by the smooth-type *mycobacterium.*

17. The method of claim 16, wherein the mRNA preferentially expressed by the smooth-type *mycobacterium* is transcribed from a gene selected from moeA1, pe13, pepR, leuC, choD, aao, fabG, tsnR, leuD, pe25 or ispD.

18. The method of claim 1, wherein the *mycobacterium* is *Mycobacterium tuberculosis.*

19. The method of claim 1, wherein the *mycobacterium* is *Mycobacterium bovis.*

* * * * *